United States Patent
Minden et al.

(10) Patent No.: US 11,655,271 B2
(45) Date of Patent: May 23, 2023

(54) PROTEIN AND PEPTIDE PURIFICATION METHODS

(71) Applicant: Carnegie Mellon University, Pittsburgh, PA (US)

(72) Inventors: Jonathan Minden, Pittsburgh, PA (US); Amber Lucas, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 16/972,923

(22) PCT Filed: Jun. 7, 2019

(86) PCT No.: PCT/US2019/036035
§ 371 (c)(1),
(2) Date: Dec. 7, 2020

(87) PCT Pub. No.: WO2019/236988
PCT Pub. Date: Dec. 12, 2019

(65) Prior Publication Data
US 2021/0253630 A1   Aug. 19, 2021

Related U.S. Application Data

(60) Provisional application No. 62/763,298, filed on Jun. 8, 2018, provisional application No. 62/919,469, filed on Mar. 14, 2019.

(51) Int. Cl.
| | | |
|---|---|---|
| *C07K 1/10* | (2006.01) | |
| *C07K 1/14* | (2006.01) | |
| *C07D 403/12* | (2006.01) | |
| *C12N 9/76* | (2006.01) | |
| *C07K 19/00* | (2006.01) | |

(52) U.S. Cl.
CPC .............. *C07K 1/14* (2013.01); *C07D 403/12* (2013.01); *C07K 1/10* (2013.01); *C12N 9/6427* (2013.01); *C07K 19/00* (2013.01); *C12Y 304/21004* (2013.01)

(58) Field of Classification Search
None
See application file for complete search history.

(56) References Cited

U.S. PATENT DOCUMENTS

| | | |
|---|---|---|
| 6,508,957 B2 | 1/2003 | Kunimoto et al. |
| 2010/0016545 A1 | 1/2010 | Wiessler et al. |
| 2016/0235716 A1 | 8/2016 | Kesicki et al. |
| 2016/0370376 A1 | 12/2016 | Polukhtin et al. |

FOREIGN PATENT DOCUMENTS

WO   2007144200 A1   12/2007

OTHER PUBLICATIONS

Kang et al., "Tetrazine litigation for chemical proteomics", Proteome Science, 2017, pp. 1-13, vol. 15, No. 15.
Maier et al., "Acid-Labile Traceless Click Linker for Protein Transduction", J. Am. Chem. Soc. 2012, pp. 10169-10173, vol. 134, No. 24.
Van Buggenum et al., "A covalent and cleavable antibody-DNA conjugation strategy for sensitive protein detection via immuno-PCR", Scientific Reports, 2016, pp. 1-12, vol. 6, No. 22675.
Atassi et al., "[49] Reaction of Proteins with Citraconic Anhydride", Methods Enzymol., 1972, pp. 546-553, vol. 25.
Butler et al., "[14] Maleylation of Amino Groups", Methods Enzymol., 1972, pp. 191-199, vol. 25.
Devaraj et al., "Fast and Sensitive Pretargeted Labeling of Cancer Cells via Tetrazine/Trans-Cyclooctene Cycloaddition", Agnew Chem Int Ed Engl., 2009, pp. 7013-7016, vol. 48:38.
Karver et al., "Synthesis and Evaluation of a Series of 1,2,4,5-Tetrazines for Bioorthogonal Conjugation", Bioconjug Chem., 2011, pp. 2263-2270, vol. 22:11.
Kirby et al., "Structure and Efficiency in Intramolecular and Enzymic Catalysis. Cataiysis of Amide Hydrolysis by the Carboxy-group of Substituted Maleamic Acids", Journal of the Chemical Society Perkin Transactions, 1972, pp. 1206-1214, vol. 2:9.
Klapper et al., "[46] Acylation with Dicarboxylic Acid Anhydrides", Methods Enzymol., 1972, pp. 531-536, vol. 25.
Oliveira et al., "Inverse electron demand Diels-Alder reactions in chemical biology", Chemical Society Reviews, 2012, pp. 1-57.
Pubchem, Substance Record for SID 315355093, 2016, pp. 1-4. Retrieved from https://pubchem.ncbi.nlm.nih.gov/substance/315355093.

*Primary Examiner* — Thomas S Heard
(74) *Attorney, Agent, or Firm* — The Webb Law Firm

(57) ABSTRACT

Provided herein are methods, reagents, and kits for isolating polypeptides, such as a proteome. Also provided herein is a modified trypsin polypeptide that is resistant to autolysis, and that can be selectively-separated from a biological sample once digestion is complete.

6 Claims, 14 Drawing Sheets

Specification includes a Sequence Listing.

```
>sp|P00761|TRYP_PIG Trypsin OS=Sus scrofa OX=9823 PE=1 SV=1
FPTDDDDKIVGGYTCAANSIPYQVSLNSGSHFCGGSLINSQWVVSAAHCYKSRIQVRLGE
HNIDVLEGNEQFINAAKIITHPNFNGNTLDNDIMLIKLSSPATLNSRVATVSLPRSCAAA
GTECLISGWGNTKSSGSSYPSLLQCLKAPVLSDSSCKSSYPGQITGNMICVGFLEGGKDS
CQGDSGGPVVCNGQLQGIVSWGYGCAQKNKPGVYTKVCNYVNWIQQTIAAN
```

(A)

(B)

(A)

(B)

US 11,655,271 B2

PROTEIN AND PEPTIDE PURIFICATION METHODS

CROSS REFERENCE TO RELATED APPLICATIONS

This application is the United States national phase of International Application No. PCT/US2019/036035 filed Jun. 7, 2019, and claims priority to U.S. Provisional Patent Application No. 62/763,298 filed Jun. 8, 2018, and U.S. Provisional Patent Application No. 62/919,469 filed Mar. 14, 2019, the disclosures of which are hereby incorporated by reference in their entirety.

STATEMENT REGARDING FEDERAL FUNDING

This invention was made with government support under Grant No. IIP-1700833 awarded by the National Science Foundation. The government has certain rights in this invention.

The Sequence Listing associated with this application is filed in electronic format via EFS-Web and is hereby incorporated by reference into the specification in its entirety. The name of the text file containing the Sequence Listing is 6526_2007137_ST25.txt. The size of the text file is 2,416 bytes, and the text file was created on Dec. 1, 2020.

Proteomics is the study of all expressed proteins in cells, tissues and organisms, where cells express thousands of different proteins at concentrations that range from hundreds of copies per cell to tens of millions of copies. A major stumbling block for proteomics research and diagnostics is sample preparation. Protein samples originate from a very wide variety of sources, each of which presents its own preparation problem. Some samples have high salt, some have high levels of DNA and RNA, some are very dilute, and some have large amounts of lipids and small organic compounds. There is no universal method for protein sample preparation.

A significant stumbling block for proteomics research and diagnostics is peptide sample preparation. A common step in peptide production is the proteolytic digestion of proteins. Trypsin is the most common proteolytic enzyme used for proteomics peptide analysis. Once the proteins are digested, the trypsin must be removed prior to mass spectrometry analysis. In addition, trypsin is prone to auto-digestion, which contaminates peptide samples with peptides arising from trypsin autolysis. These trypsin autolysis peptides can strongly interfere with proteomic sample analysis.

Improved methods are desired for preparation of protein samples for proteomics.

SUMMARY

According to one aspect or embodiment of the invention, provided herein is a compound comprising a member of a bio-orthogonal coupling pair linked to a dicarboxylic anhydride moiety.

According to another aspect of the invention, a modified trypsin polypeptide is provided. The modified trypsin polypeptide, comprising: a trypsin polypeptide; biotin moieties attached to the trypsin polypeptide; and groups comprising a member of a bio-orthogonal coupling pair attached to the trypsin polypeptide, wherein the ratio of groups comprising a member of a bio-orthogonal coupling pair to biotin moieties on the trypsin polypeptide ranges from 1:4 to 1:6. Also provided is a method of preparing tryptic polypeptide fragments, comprising digesting a polypeptide with the modified trypsin polypeptide.

In yet another aspect or embodiment of the invention, a protein or peptide isolation kit is provided, comprising the compound of any one of claims 1-13 in a vessel, or the modified trypsin polypeptide of claim 14 or 15 in a vessel in packaging.

According to another aspect or embodiment of the invention, a method of purifying a polypeptide is provided, comprising:
  mixing a sample having a basic pH, comprising a polypeptide with an amount of a coupling compound comprising a moiety comprising a first member of a bio-orthogonal coupling pair linked by a linker to a maleic anhydride moiety; coupling polypeptides in the sample to a second member of the bio-orthogonal coupling pair linked to a substrate;
  optionally washing polypeptides bound to the substrate to remove any unbound materials from the substrate-bound polypeptides; and
  eluting the polypeptides from the substrate in an elution solution having an acidic pH.

In another aspect or embodiment, a method of preparing a modified trypsin polypeptide is provided, comprising conjugating a trypsin polypeptide with a first compound comprising an amine-reactive moiety, or a sulfhydryl-reactive moiety linked to biotin, and a second compound comprising an amine-reactive moiety, or a sulfhydryl-reactive moiety linked to a first member of a bio-orthogonal coupling pair in a molar ratio of the first compound to the second compound ranges from 4:1 to 6:1.

BRIEF DESCRIPTION OF THE DRAWINGS

FIG. 2A shows the first half of the reaction where mTet-CDM is coupled to any protein or peptide and then is combined with TCO-beads.

FIG. 2B shows the second half of the process where mTet-CDM-coupled protein/peptide is coupled to TCO-beads, contaminants are washed away, and finally the CDM linkage to protein/peptide is reversed at slightly acidic pH.

DETAILED DESCRIPTION

Figure 1A:
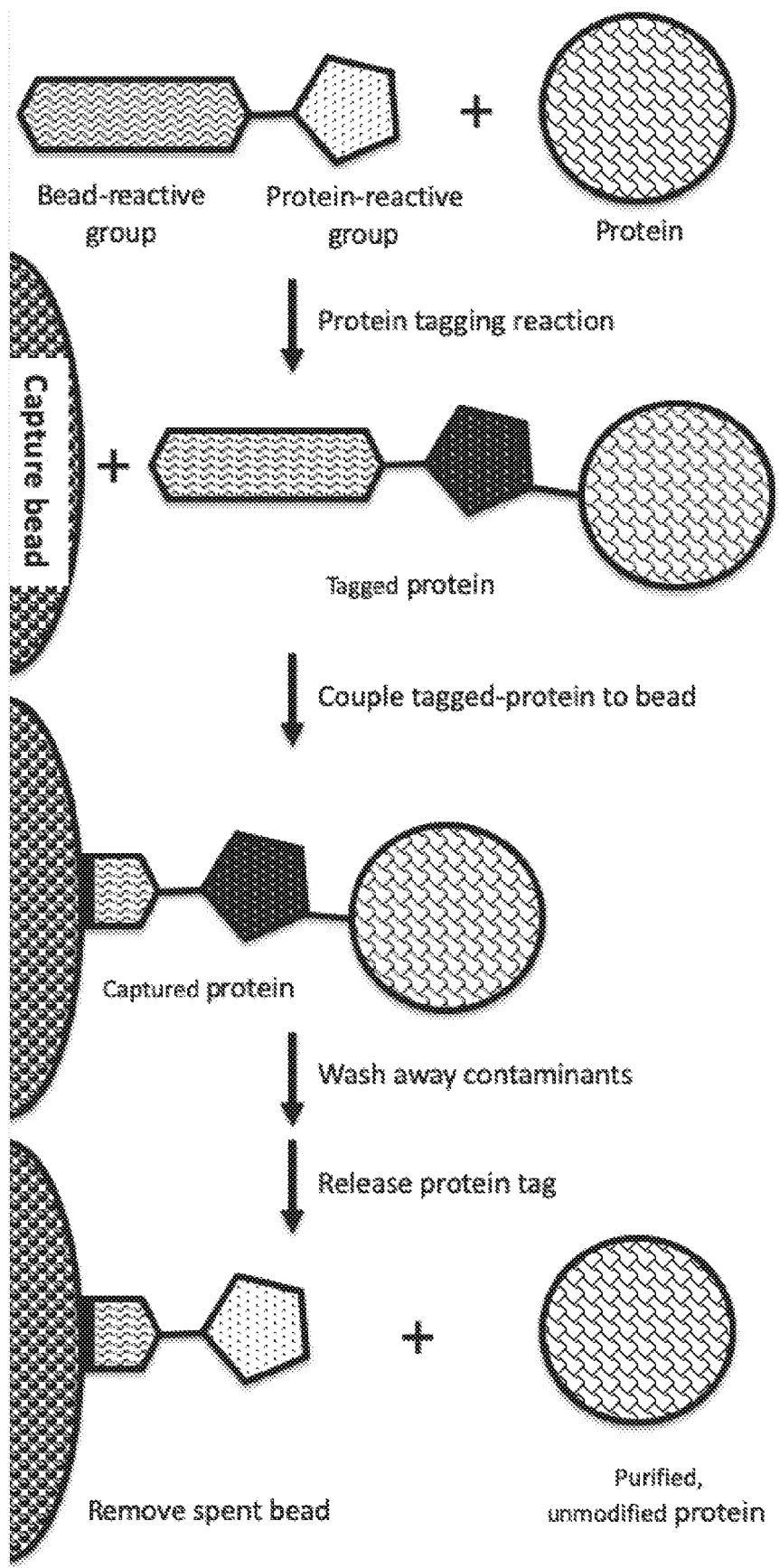
FIGS. 1A and 1B show schematically non-limiting examples of protein or polypeptide purification methods as described herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more. A patient is a human or non-human animal.

As used herein, the term "comprising" is open-ended and may be synonymous with "including", "containing", or "characterized by". As used herein, embodiments "comprising" one or more stated elements or steps also include, but are not limited to embodiments "consisting essentially of" and "consisting of" these stated elements or steps.

A "moiety" (pl. "moieties") is a part of a chemical compound, and includes groups, such as functional groups. As such, a nucleobase moiety is a nucleobase that is modified by attachment to another compound moiety, such as a polymer monomer, e.g. the nucleic acid or nucleic acid analog monomers described herein, or a polymer, such as a nucleic acid or nucleic acid analog as described herein.

"Alkyl" refers to straight, branched chain, or cyclic hydrocarbon groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—$CH_2$—$CH_2$—). "Optionally substituted alkylene" refers to alkylene or substituted alkylene.

"Alkene or alkenyl" refers to straight, branched chain, or cyclic hydrocarbyl groups including from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein. "Optionally substituted alkene" refers to alkene or substituted alkene. Likewise, "alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Cycloalkyl" refer to monocyclic, bicyclic, tricyclic, or polycyclic, 3- to 14-membered ring systems, which are either saturated, unsaturated or aromatic. "Cycloalkenyl" refer to monocyclic, bicyclic, tricyclic, or polycyclic, 3- to 14-membered ring systems, which comprise at least one carbon-to-carbon double bond in the ring system. The cycloalkyl group may be attached via any atom. Cycloalkyl also contemplates fused rings wherein the cycloalkyl is fused to an aryl or hetroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with 1, 2 or 3 substituents, attached at any available atom to produce a stable compound.

As used herein a "polypeptide" includes proteins and oligopeptides as a class, and generally refers to a polypeptide comprising two or more amino acid residues, though typically referring to longer amino acid chains.

A "sample" comprising a polypeptide may be blood, plasma, serum, urine, cerebrospinal fluid, cell lysate, cell culture medium, or any other biological composition comprising a polypeptide. In one embodiment, the sample is a cell lysate from a sample of a patient's tissue. In another embodiment, the sample is prepared by lysing pelleted cells from a cell culture, e.g., to produce a recombinant protein or to analyze the proteome of cells of a cell, tissue, or organ culture.

A linker is a moiety in a compound that connects one moiety to another. An "inert" linker is a moiety that covalently attaches, and optionally spaces, one moiety in a compound from another and which no substantial negative effect on the activity of the overall compound, e.g., in context of the present invention, the ability of the reactive groups, such as a tetrazine group, a succidimidyl group, or a dicarboxylic acid anhydride groups, such as maleic anhydride to react with their intended targets, and form and maintain a bond according to the methods described herein. Aside from serving to covalently-link two moieties, a linker may have a beneficial effect, such as in the physical separation of moieties to which it is attached, e.g., to optimize spacing to avoid steric effects. A linker also may serve some additional function, such as altering the hydrophobicity/hydrophilicity of the overall molecule, to provide an additional site, e.g., an amine protected by a protective group for linking additional moieties to the compound, or to rigidize the overall molecule. A linker is attached to the remainder of the compound by any suitable linkage moiety ("linkage"), e.g., by a carbon-carbon bond, an ester, a thioester, an amine, an ether, an amide, a carbonate, or a carbamate linkage to the additional moieties of the compound. The linker may be hydrocarbyl, that is including only carbons and hydrogens, or optionally comprising one or more hetero-atom, such as N, O, and/or S. In the context of the present invention, in one embodiment, one suitable linker is a divalent moiety comprising a PEG group —(O—CH$_2$—CH$_2$)$_n$—, where n ranges from 2 to 100, e.g., from 2-10 (PEG$_{2-10}$), or from 2-5 (PEG$_{2-5}$) such as 2, 3, 4 (PEG$_4$), 5, 6, 7, 8, 9, or 10. A PEG linker may comprise one or more methylene groups at either end in addition to a suitable linkages attaching the PEG group to the tetrazine and dicarboxylic anhydride moieties, e.g. maleic anhydride moieties.

In one aspect or embodiment of the present invention, a compound is provided comprising a first member of a bio-orthogonal coupling pair, such as a tetrazine moiety, linked to a dicarboxylic anhydride moiety. Dicarboxylic acid anhydrides, such as maleic anhydrides, e.g. citraconic anhydride, have been used in the conjugation of proteins (see, e.g., Klapper M L and I M Klotz, [46] Acylation with Dicarboxylic Acid Anhydrides Methods Enzymol. 1972; 25:531-6; Atassi M Z and A F Habeeb, [49] Reaction of proteins with citraconic anhydride Methods Enzymol. 1972; 25:546-53; Butler P J, Hartley B S [14] Maleylation of amino groups Methods Enzymol. 1972; 25:191-9; A. J. Kirby and P. W. Lancaster, Structure and efficiency in intramolecular and enzymic catalysis. Catalysis of amide hydrolysis by the carboxy-group of substituted maleamic acids Journal of the Chemical Society Perkin Transactions 2 2(9) January 1972). The first member of a bio-orthogonal coupling pair, such as a tetrazine moiety, is linked to the dicarboxylic anhydride to produce a compound useful in the purification of polypeptides.

In use, after linking of the compound to polypeptides by the formation of an amide bond between the dicarboxylic anhydride of the compound and primary amines of the polypeptide, the first member of the bio-orthogonal coupling pair is reacted with a second member of the bio-orthogonal coupling pair that is linked to a substrate, such as beads, a porous, or a solid surface, producing a substrate-bound polypeptide (e.g. protein or peptide). The reaction of the dicarboxylic anhydride moiety with primary amines of a polypeptide will result in the formation of an acid-labile amide bond. Mild acids (e.g. with a pH ranging from >2 to 6) will cleave the amide bond of the conjugate, such that the polypeptides can be eluted. As such, a wash solution for washing any cellular component from the polypeptides, that does not cleave the amide bond between the substrate and the bound polypeptides may be suitable for the purpose of washing the polypeptides.

It should be recognized that some non-proteinaceous compounds present in a sample might also comprise a primary amine and can be purified along with the polypeptides. Nevertheless, for purposes of most proteomic assays, this non-proteinaceous contamination is not expected to significantly impact the assay. As such, by purification, it is meant the enrichment of one or more constituents in a sample by removal of other constituent(s) from the sample. It should be understood that in embodiments, the process of purification of polypeptides or proteins effectively separates the polypeptides from other cellular materials, such as nucleic acids, carbohydrates and lipids, by, e.g., washing substrate bound polypeptides with suitable wash solutions, e.g. water, saline, TRIS-EDTA, PBS, etc. under conditions such that the polypeptides are not eluted from the column.

In one aspect, the polypeptides are bound to a chromatography column substrate, such as a porous matrix or beads, such that washing, and elution can be carried out in a single chromatography column (see, e.g., FIG. 1A). A chromatography column is any container able to retain the substrate and allows passage of a solution through the substrate without loss of the substrate. A chromatography column is typically a tube with a retaining mesh or screen.

In another aspect of the present invention a protein or polypeptide purification method is provided. This method is universal as it targets only primary amines present at the N-terminus of all polypeptides, and lysine residues. Any biological sample may be used, such as a biological sample obtained from a patient, or a cell, tissue, or organ culture, a biopsy, pelleted cells from any biological fluid sample, such as urine, blood, saliva, mucus, cerebrospinal fluid, semen, aspirate, a tissue culture for production of a recombinant protein, etc. In the method, a cell lysate is prepared, e.g., by use of any suitable method, as are broadly-known, e.g. by homogenization, optionally in the presence of any suitable salts, buffers, surfactants, emulsifiers, chaotropic agents, chelating agents, etc., e.g., in urea, SDS or RIPA buffer. In one aspect the cell lysate is prepared in a mildly-basic buffer or salt solution, e.g., to produce a lysate having a pH ranging from >7 to 10, e.g., ranging from 8 to 9.5. The sample may be cell-free, and may not require lysing, such as in the case of analyzing a secretome, in the production of a recombinant protein that is secreted into the medium, or in the analysis of cell-free preparations (e.g. centrifuged supernatants) of biological fluids.

If cell lysates are to be analyzed, once cells are lysed, if needed, the pH of the lysate is adjusted using, e.g., salts or buffer solutions, to a pH ranging from >7 to 10, e.g., ranging from 8 to 9.5. The lysate is mixed with the compound comprising a first member of a biorthogonal coupling pair, such as a tetrazine moiety, linked to a dicarboxylic anhydride moiety, such as, for example and without limitation mTET-PEG$_4$-CDM. The sample is then reacted with a substrate having a second member of the bio-orthogonal coupling pair, such as TCO, attached thereto. The second member of the bio-orthogonal coupling pair may be attached to the substrate by any suitable chemistry, e.g., coupled by NHS to primary amines of a substrate. The substrate may be a bead, such as, for example and without limitation, a magnetic bead, an agarose bead, a plastic or glass surface (e.g. a well of a multi-well plate, such as a 96-well plate), or a porous matrix. The substrate may comprise any suitable substrate material that does not interfere to any substantial extent with the reactions and processes as described herein. The substrate may be contained in a chromatography column, a spin column, or in any other physical form that retains the substrate while it polypeptides are coupled, washed, and eluted, as are broadly-known in the biological and chemical arts. Magnetic beads are processed in any art-recognized manner.

The polypeptide-bound substrate is then washed using any suitable wash solution that is not acidic, e.g. having a pH of 6.0 or less, to prevent premature hydrolysis of the amide bond attaching the polypeptides to the substrate. Suitable wash solutions include, without limitation: water, saline, PBS, Tris-EDTA, or other salt solutions or buffered salt solutions that do not hydrolyze the amide bond attaching the polypeptides to the substrate. The substrate may be washed one or more times in an art-recognized manner for any selected substrate. Two or more wash steps, with the same or different wash solutions may be applied.

Figure 1B:
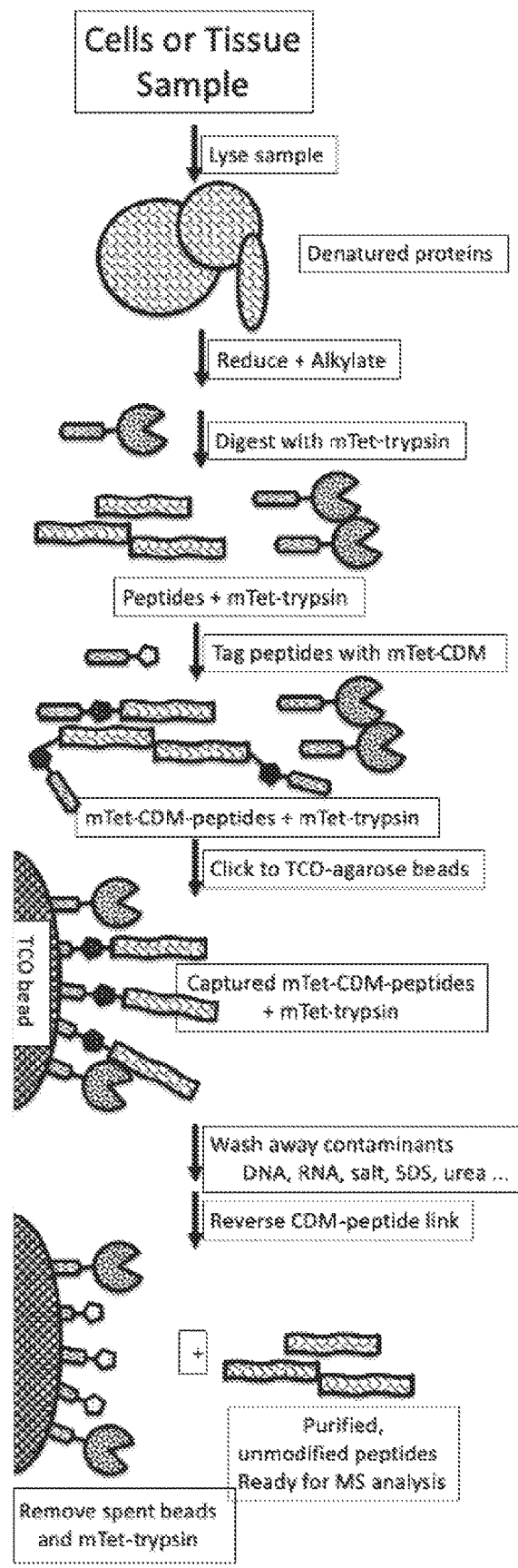

In a variation of the method described above and shown in FIG. 1A, peptides are purified, rather than whole proteins, are purified. This is depicted schematically in FIG. 1B. Briefly, a proteinase digestion step is added after lysis of the cells or tissue. In one embodiment, the proteinase is trypsin, and in another, the proteinase is modified trypsin as described below.

Once the polypeptide-bound substrate is washed, the polypeptides are eluted from the substrate using a mildly-acidic elution solution. The composition of the elution solution may vary, depending on the desired end use for the eluted polypeptides. The elution solution may have a pH ranging from 2 to <7, or from 2.5 to 6. By use of carboxylic anhydride coupling to amines of the polypeptides, once the amide bond coupling the polypeptides to the substrate are cleaved, the primary amines of the polypeptides are restored.

"Click Chemistry" describes reactions that are high yielding, wide in scope, create only byproducts that can be removed without chromatography, are stereospecific, simple to perform, and can be conducted in easily removable or benign solvents. In the context of the present disclosure a click chemistry reaction is biorthogonal, meaning it is sufficiently selective that it can be performed reliably even in a complex biological environment. These reactions must proceed efficiently in the presence of the multitude of functional groups found in living systems such nucleophiles, electrophiles, reductants, oxidants, and water. Simultaneously, these reactions should have a minimal impact on the biology itself.

In the context of bio-orthogonal reactions, e.g., a bio-orthogonal click chemistry reaction, relies on bond formation between molecules or moieties not found in natural compounds, referred to herein as bio-orthogonal coupling pairs. Such reactions are preferably: selective over other potential reactive functional groups present on biomolecules, proceed in aqueous media at near physiological pH, and have fast reaction rates at room temperature (or up to 37° C.) using low reactant concentrations, all to ensure high modification efficiency (Lopes Bernardes, G., Oliveira, B., & Guo, Z. (2017). Inverse electron demand Diels-Alder reactions in chemical biology. Chemical Society Reviews https://doi.org/10.17863/CAM.10698). Bio-orthogonal reaction reagents (bio-orthogonal coupling pairs) do not react with natural cellular products, such as proteins or nucleic acids. Coupling occurs under a wide range of aqueous conditions and are stable once formed. In one embodiment, the bio-orthogonal reaction is an inverse-electron-demand Diels-Alder reaction (IEDDA, e.g., inverse electron demand [4+2] Diels-Alder cycloaddition), in which an electron-rich dienophile reacts (e.g., a strained alkene) with an electron-poor diene (e.g., a tetrazine such as a 1,2,4,5-tetrazine or a 4-(1,2,4,5-tetrazinyl)phenyl moiety such as 4-(1,2,4,5-tetrazin-3-yl)phenyl, 6-alkyl-1,2,4,5-tetrazine, 6-pyridin-2-yl-1,2,4,5-tetrazine, 6-pyrimidin-2-yl-1,2,4,5-tetrazine, 4-(6-alkyl-1,2,4,5-tetrazin-3-yl)phenyl, 4-(6-pyridin-2-yl-1,2,4,5-tetrazin-3-yl)phenyl, or 4-(6-pyrimidin-2-yl-1,2,4,5-tetrazin-3-yl)phenyl, where alkyl may be a $C_{1-4}$ alkyl group) (see, e.g., Karver, M R, et al., Synthesis and Evaluation of a Series of 1,2,4,5-tetrazines for Bio-orthogonal Conjugation. *Bioconjug Chem.* 2011 Nov. 16; 22(11):2263-2270) in contrast to a normal electron demand Diels-Alder reaction, where an electron-rich diene reacts with an electron-poor dienophile (see, e.g., Lopes Bernardes, G., Oliveira, B., & Guo, Z. (2017). Chemical Society Reviews https://doi.org/10.17863/CAM.10698 for further details, as well as providing examples of other bio-orthogonal reactions). Of note "1,2,4,5-tetrazine" refers to the precise 1,2,4,5-tetrazine compound or a 1,2,4,5-tetrazinyl moiety, while "a 1,2,4,5-tetrazine" refers to a compound or moiety comprising the 1,2,4,5-tetrazinyl moiety. In another example, the bio-orthogonal coupling pair is an alkyne-azide coupling pair, such as a propargyl moiety and an azido moiety, as are broadly-known.

In IEDDA reactions, Electron-poor dienes, such as 1,2,4,5-tetrazines, are reacted with an electron-rich dienophile, for example, a strained dienophile, and fine-tuning the choice of electron-poor diene and electron-rich dienophile ("IEDDA coupling pair") can be used to tailor the reaction kinetics (Id.). non-limiting examples of suitable electron-poor dienes for IEDDA reactions include: tetrazines, such as 1,2,4,5 tetrazines, e.g. methyltetrazine and triazines (see, e.g., Devaraj, N K, et al., Fast and Sensitive Pretargeted Labeling of Cancer Cells via Tetrazine/Trans-Cyclooctene Cycloaddition *Agnew Chem Int Ed Engl.* 2009; 48(38):7013-7016 and Karver, M R, et al., *Bioconjug Chem.* 2011 Nov. 16; 22(11):2263-2270). A non-limiting example of an electron-rich dienophile for IEDDA reactions is trans-cyclooctene. One non-limiting example of a bio-orthogonal reaction and reaction pair is the reaction of methyl-tetrazine (mTet) and trans-cyclooctene (TCO). That IEDDA pair was used because of the fast reaction kinetics and the reaction does not need a catalyst. In the example below, an NHS-ester with PEG spacers (linkers) of each of these reagents, was used to allow diffusion of mTet-CDM-proteins/mTet-CDM-peptide/ free mTet-CDM deep into the polymer shell surrounding the beads. Other suitable bio-orthogonal coupling reactions include alkyne-azide reactions, e.g. with a triazide and an alkyne, or alkyne-DBCO (dibenzocyclooctyne) reactions.

Methods provided herein described herein is the use of click chemistry to enable protein and peptide cleanup. First, an mTet derivative of the reversible protein tag, called mTet-CDM is synthesized. mTet-CDM is a very effective capture reagent, but excess unused mTet-CDM needs to be removed. mTet is one half of a bi-orthogonal coupling pair. The other half of the pair is TCO. Neither mTet nor TCO react with other biological compounds and are therefore considered bio-orthogonal. As such, their reaction is extremely specific, giving no side products.

Figure 2A:
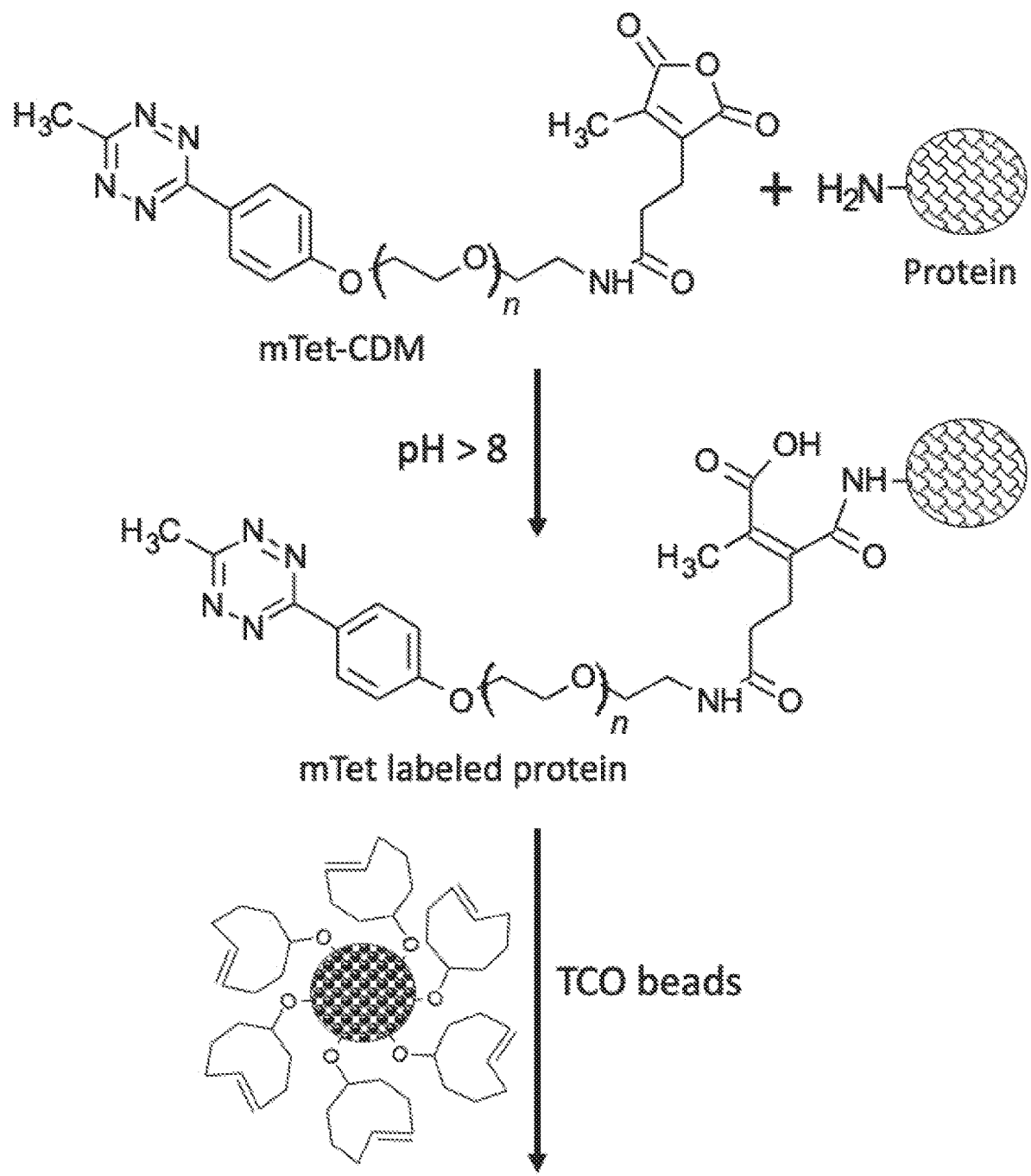
FIGS. 2A and 2B illustrate the process for protein/peptide cleanup using mTet-CDM and TCO-beads.
Figure 2B:
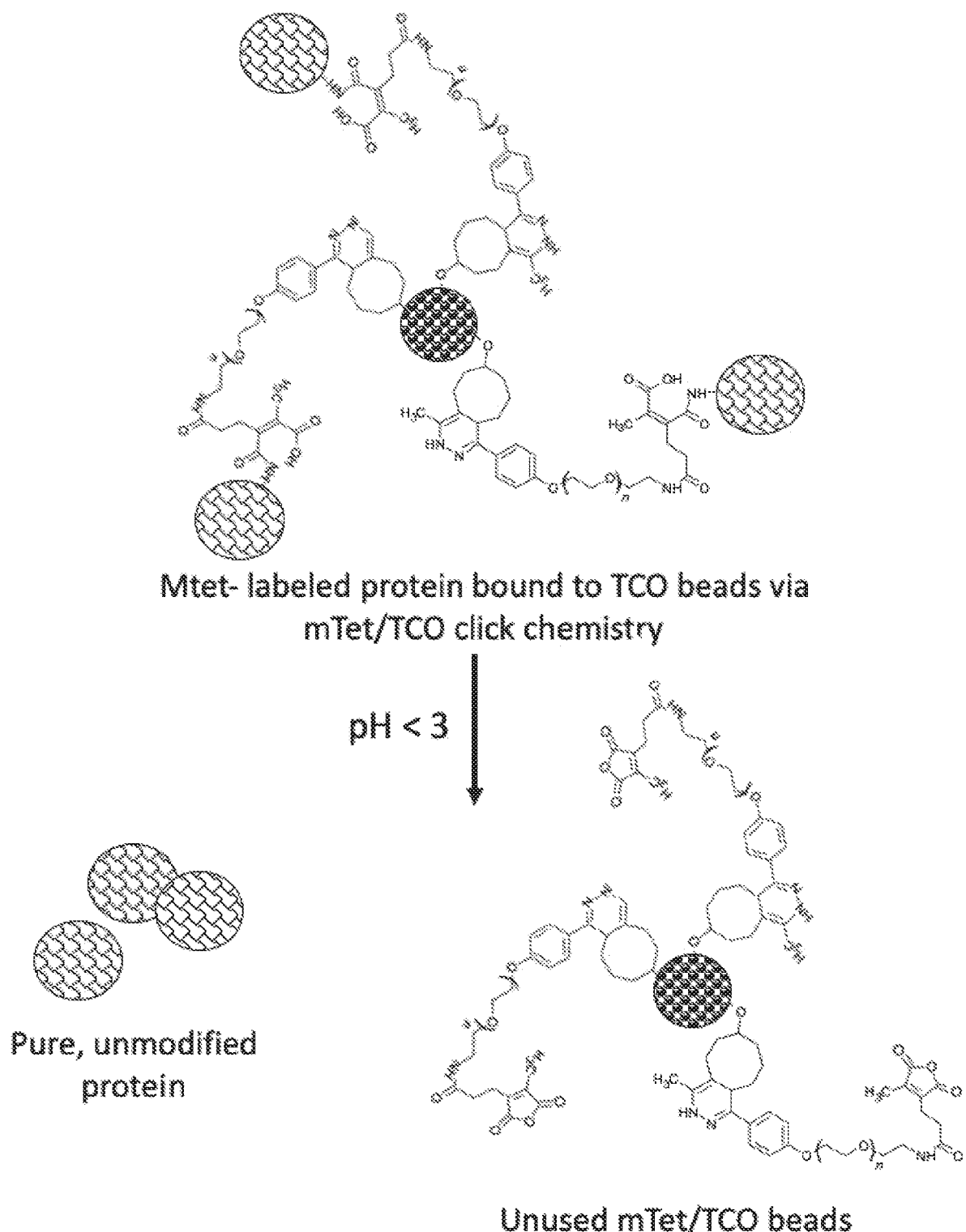

In examples of the method, to capture both free mTet-CDM and mTet-CDM coupled to proteins or peptides, beads with bound TCO are used. The composition of the beads may be non-magnetic or magnetic beads. The beads with bound TCO may be made by reacting TCO-NHS ester with amine-derivatized beads. Since the normal density of TCO molecules on commercial amine-beads may be too low for the purpose described herein, the commercial beads may be modified to carry 10-50 times more amino groups by growing amine-containing polymers from the surface of the beads. These amine groups are then coupled to TCO, hence the beads will carry 50 times more TCO. The process for protein/peptide cleanup is using mTet-CDM and TCO-beads is shown in FIG. 2.

Proteases, such as trypsin, play an important role in proteomics and biochemistry. Trypsin cleaves proteins on the carboxyterminal side of lysine and arginine residues, except if there is an adjacent proline. This cleavage specificity allows researchers to identify the genes that encode individual proteins based on predicted trypsin cleavage patterns. The protein cleavage products, known as tryptic peptides, are introduced into a mass spectrometer (MS) that precisely determines the mass of the tryptic peptides. MS is also capable of determining the amino acid sequence of the tryptic peptides to further characterize the protein(s) being studied.

Figures 3, 4:
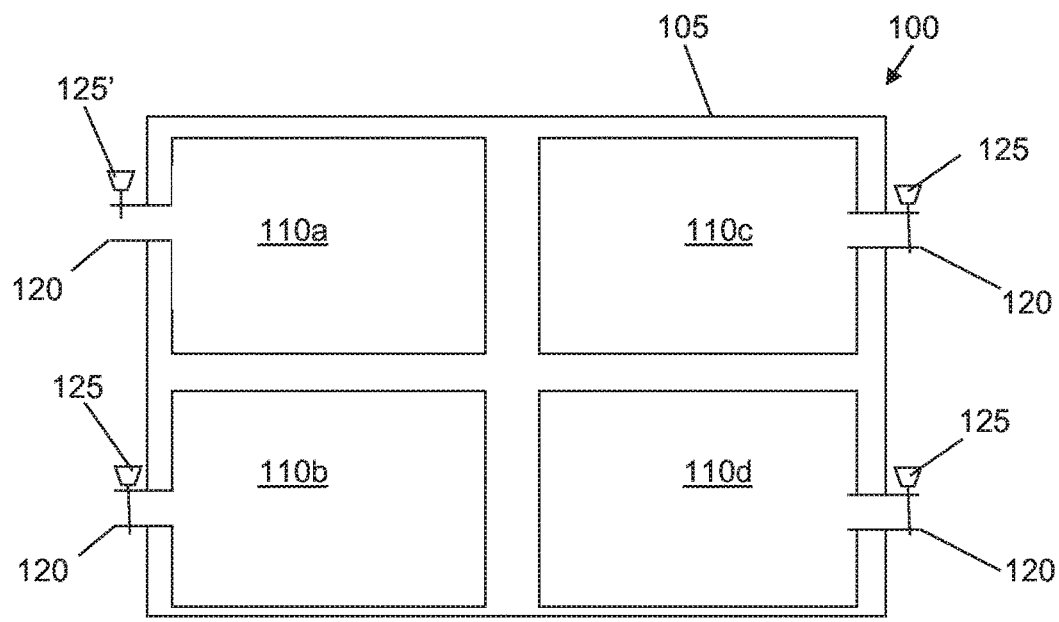
FIG. 3 provides an exemplary sequence of a trypsin polypeptide (SEQ ID NO: 1).
FIG. 4 is a schematic depiction of an exemplary cartridge.

Trypsin is a broadly-known, well-studied acid protease. An exemplary trypsin protein sequence (precursor) is shown in FIG. 3. By "a trypsin polypeptide", it is meant any natural trypsin or a proteolytically-active variant thereof. A large number of trypsins and modified trypsins differing in sequence from natural trypsin are known and/or are commercially-available, including sequence variants of natural trypsin. Trypsin is commonly-used for proteomic studies, producing tryptic peptides, that can be analyzed by a variety of methods, such as mass spectroscopy or Edman sequencing. In practice, trypsin autolyses, resulting in the potential of the autolysis products obscuring peptides resulting from the protein sample to be digested, and also resulting in the production of pseudotrypsin, which exhibits a broadened specificity including a chymotrypsin-like activity. To circumvent these issues, typical trypsin digestions are done at low trypsin-to-target protein ratios at about 1:20 to 1:50. Further, it is desirable to remove the trypsin from the protein fragments after digestion. Trypsin comprises a number of primary amines, e.g., Lys residues, and its N-terminus. The primary amine of lysine can be used to attach groups using any useful chemistry, such as NHS linkers. Trypsin has 14 lysine residues, and only two arginine residues, the other target for autolysis. NHS-biotin, e.g., an N-hydroxy succinimidyl ester of biotin (See below), can be used to modify trypsin at lysine residues and at the N-terminus. Further, it does not assist in the complete removal of trypsin from a protein sample, as NHS-biotin does not completely label trypsin.

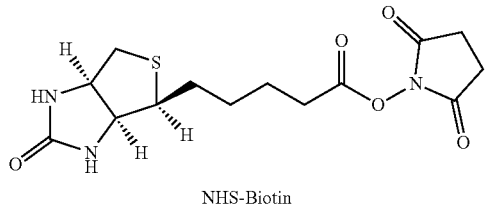 [SMILES: O=C1N[C@H]2[C@H](CS[C@H]2CCCCC(=O)ON2C(=O)CCC2=O)N1]

NHS-Biotin

Described herein is a method of removing trypsin from peptide samples. The method described herein results in a derivative of trypsin that is highly resistant to autodigestion and that can be removed from solution by chemically crosslinking the trypsin derivative to a solid support matrix using bio-orthogonal "Click" chemistry. As above, trypsin contains 14 lysine residues and only two arginine residues. Thus, the majority of autodigestion sites are at lysine residues.

In the examples, below, to limit autodigestion, >95% of all lysines (plus the amino terminus) were coupled with a mixture of methyltetrazine-$PEG_4$-NHS and biotin-NHS. Biotin-NHS alone does not diminish the reactivity of trypsin, while extensive labeling with methyltetrazine-$PEG_4$-NHS alone causes protein insolubility and total loss of enzymatic activity. Combining these two labeling reagents at a molar ratio of methyltetrazine-$PEG_4$-NHS to biotin-NHS at 1:5 allows for complete preservation of trypsin activity. This trypsin derivative is referred to herein as MB-Trypsin. The presence of methyltetrazine on the MB-Trypsin allows for the near complete removal of this protein from solution by coupling to beads containing trans-cyclooctene (TCO). Together, methyltetrazine and TCO form a bio-orthogonal coupling pair where these two moieties react to form a covalent linkage at very rapid rates. Other tetrazinyl moieties may be employed in this click chemistry pair, or other bio-orthogonal click chemistry pairs may be employed in the linking of trypsin to a substrate, such as a bead, for removal.

In use, the modified trypsin, having both pendant biotin moieties and pendant groups comprising a first member of a bio-orthogonal coupling pair, such as tetrazinyl, e.g. methyltetrazinyl moieties, for example in a molar ratio ranging from 4:1 (biotin:bio-orthogonal coupling pair member) to 6:1, e.g. 5:1, as described herein, is used to digest a protein sample. After sample digestion, the digest is contacted with a surface-bound, e.g., bead-bound second member of the bio-orthogonal coupling pair (e.g., click-chemistry partner) of the first member of the bio-orthogonal coupling pair. For example, in the case of tetrazine as the first member of the bio-orthogonal coupling pair, trans-cyclooctene, or another strained cycloalkene, e.g., of 8 or more carbons may be the surface-bound second member of the bio-orthogonal coupling pair.

As such, according to embodiments of the invention, trypsin is modified with both biotin linked to an amine- or sulfhydryl-reactive moiety, such as NHS, malemide, or iodoacetamide moiety and a first member of a bio-orthogonal coupling pair linked to an amine- or sulfhydryl-reactive moiety, for example and without limitation an NHS-biotin and an NHS-tetrazinyl compound. In embodiments, the NHS-tetrazinyl compound comprises a tetrazinyl moiety linked to an NHS moiety, e.g., having the structure:

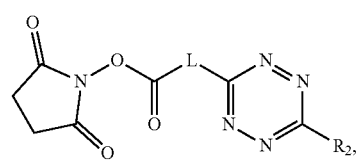

where $R_2$ is H or $C_{1-3}$ alkyl; and L is an inert linker, or

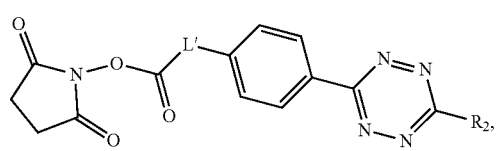

wherein L' is an inert linker, and optionally comprises an ester linkage attaching the N-succinimidyl moiety. In a further embodiment, the compound has the structure:

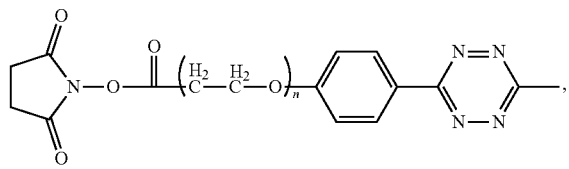

wherein n ranges from 2 to 10, e.g., 2, 3, 4, 5, 6, 7, 8, 9, or 10.

When reacted with a primary amine, such as a protein, the NHS-tetrazinyl compound leaves an amide-tetrazinyl moiety, such as:

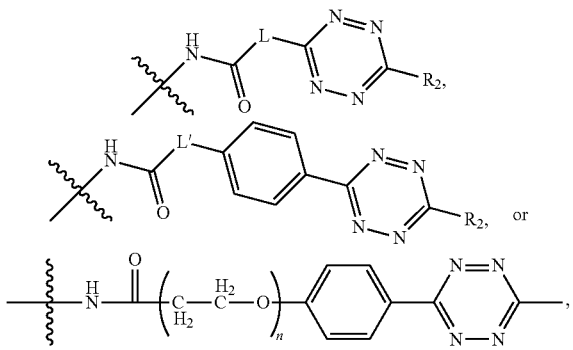

referring to the structures above. Likewise, NHS biotin (structure below) will react with a primary amine of a polypeptide, leaving an amide-biotin moiety.

The molar ratio of the first member of a bio-orthogonal coupling pair linked to an amine- or sulfhydryl-reactive moiety to biotin linked to an amine- or sulfhydryl-reactive moiety, e.g., the NHS-tetrazinyl compound to the NHS-biotin, that is reacted with trypsin, or the ratio of the first member of a bio-orthogonal coupling pair linked to an amine- or sulfhydryl-reactive moiety to biotin linked to an amine- or sulfhydryl-reactive moiety, e.g., the NHS-tetrazinyl residues to NHS-biotin residues (that is, for example, the molar ratio of amido-tetrazinyl moieties to amido-biotin moieties) attached to a trypsin polypeptide ranges from 1:4 to 1:6. With respect to the use of NHS-biotin and the NHS-tetrazinyl compound to modify trypsin, higher amounts of biotin results in failure of the NHS-tetrazinyl compound to modify a significant number of trypsin polypeptides, resulting in less effective capture of the protein. Higher amounts of the NHS-tetrazinyl compound will precipitate the trypsin in an aqueous environment.

In one aspect of the invention, a protein purification method and protein purification kit are provided. Because of the vast chemical diversity of proteins within a proteome, a standardized protein isolation method that captures the entire proteome has been historically challenging. Long standing precipitation methods rely on the hydrophobic nature of unfolded proteins, however some proteins are not sufficiently hydrophobic to precipitate, while others are too hydrophobic to go back into solution. Therefore, a universal protein cleanup method and kit described below herein include the following features:

(1) Bead-based: Protein precipitation has several problems as listed above. In addition, the need for centrifugation limits its utility for automation. Bead-based methods offer large surface areas to avoid protein precipitation problems and is automatable.

(2) Cell lysis procedure tolerance: The methods and reagents described herein accommodate many lysis methods. Many researchers prefer to maintain their protein samples in their native state for a variety of purposes. Thus, methods and reagents described herein are able to purify protein samples in either native or denatured states.

(3) Identifies a universal protein feature for targeting: Protein precipitation methods and bead capture methods rely upon general protein features such as hydrophobicity and charge, while peptide isolation methods rely on hydrophobicity, charge and size. Proteins and peptides exhibit very broad spectrum of hydrophobicity, charge and size. Therefore, targeting these qualities will not select all proteins/peptides. One feature that all proteins and peptides have in common are aliphatic primary amines (amino termini and lysine residues). Nucleic acids do not have aliphatic primary amines; carbohydrates have very few primary amines. Thus, targeting primary amines has the best potential for capturing the entire proteome.

(4) Use molecular tags rather than direct coupling to beads: Attaching proteins directly to beads via their amine groups requires a large excess of beads because the coupling reactions are not very efficient due to the intrinsic hydrolysis rate of amine-reactive coupling reagents. This large volume of beads will necessitate using large volumes of buffer to completely elute the bound proteins/peptides, yielding dilute solutions that will require extra steps to concentrate the eluted sample, which poses additional problems. Instead, the methods and reagents described herein use a molecular tag, where one end of the tag couples to primary amines on the protein or peptide and the other end of the tag directs the binding of tagged proteins/peptides to the beads.

(5) Use Click chemistry to covalently link tagged proteins/peptide to the beads: Because the CDM half of the tag forms a reversible covalent bond, click chemistry is used to form a stable covalent linkage between the tag and the bead. In particular, the Click chemistry pair of methyl-tetrazine (mTet) and trans-cycloctene (TCO), were chosen for the examples below, because of their bio-orthogonal reactivity (non-reactive with bio-molecules), they have fast reaction kinetics, they do not require a copper catalyst like other click pairs, and they are able to couple under the relatively harsh conditions of typical cell/tissue lysis procedures and withstand the stringent washing steps required to remove non-protein contaminants.

(6) Binding of all Click-CDM (free and protein/peptide bound): A feature of the protein cleanup methods, reagents and kit is to produce suitably concentrated protein/peptide samples for further biochemical or proteomic analysis. An appropriate small volume of beads used in the method to bind both free, un-reacted tags and the tagged proteins/peptides.

In another aspect of the invention, a kit is provided for use either in digesting polypeptides, or for purifying proteins or polypeptides. A kit comprises packaging and at least stated components of the kit. Packaging may be any suitable container, such as a box, sleeve, tube, carton, pouch, bag, etc., suitable for storage and/or delivery of the kit components. A "kit" may comprise one or more individual containers for the elements of the kit, though in one embodiment, all components of a kit are packaged together, or are packaged in a single container. For reagents or compositions, e.g. the reagents and compositions described herein, the kit comprises one or more vessels containing stated reagent(s) or composition(s). A kit may comprise the modified trypsin, according to any embodiment presented herein, a coupling compound, such as the compound comprising a member of a bio-orthogonal coupling pair, e.g., an electron-poor diene or an electron-rich dienophile member of an IEDDA coupling pair, such as a tetrazine moiety or a TCO moiety, or an alkyne-azide pair, linked to a dicarboxylic anhydride moiety. A substrate coupled to a second member of a bio-orthogonal coupling pair. The substrate may be in any suitable form, such as in the form of magnetic beads, beads or a porous matrix in a chromatography column, or a solid surface, such as a well of a multi-well plate. Additional vessels comprising, for example, one or more of: a digestion solution, a coupling solution, one or more wash solutions, an elution solution may be included in the kit, optionally in concentrated form, e.g., as a 2×, 5×, 10× or 25× concentrate.

The vessels of the kit may be a compartment in a cartridge for use in an automated, or semi-automated device or system for digesting and/or purifying proteins in a sample.

FIG. 4 depicts schematically a cartridge 100 comprising a housing 105, four compartments 110a, 110b, 110c, 110d, outlets 120, closed valves 125 and open valve 125'. The housing 105 may have any useful configuration and is adapted to insert into an automated device or system for controlling delivery of compositions contained within compartments 110a, 110b, 110c, 110d. Each compartment may contain a different reagent or composition, or the same reagent or composition. Valves 125 and 125' may be controlled by any suitable mechanical or electromechanical mechanism, such as by solenoids and may be placed at any point in or external to the cartridge 100, for example, the outlets may fluidly couple with the valves, which are part of the device into which the cartridge 100 inserts. The cartridge 100 depicted in FIG. 4 is merely exemplary and may comprise any number of compartments, any shape, any fluid path, and any fluid control mechanism. A person of ordinary skill in the engineering arts can configure a suitable cartridge for use in any device or system, such as an automated system. Control of the cartridge and/or reagents or compositions removed from the cartridge, may be automated, e.g., controlled by a computer-implemented process.

Example 1—Universal Protein/Peptide Isolation and Cleanup

An exemplary universal protein/peptide isolation and cleanup kit includes any or all the following reagents: TCO magnetic beads or TCO-non-magnetic beads; mTet-CDM; cell lysis buffers; wash buffer to remove non-protein contaminants; and elution buffer to reverse the CDM-protein/peptide linkage and recover purified protein/peptide sample.

Figure 5:
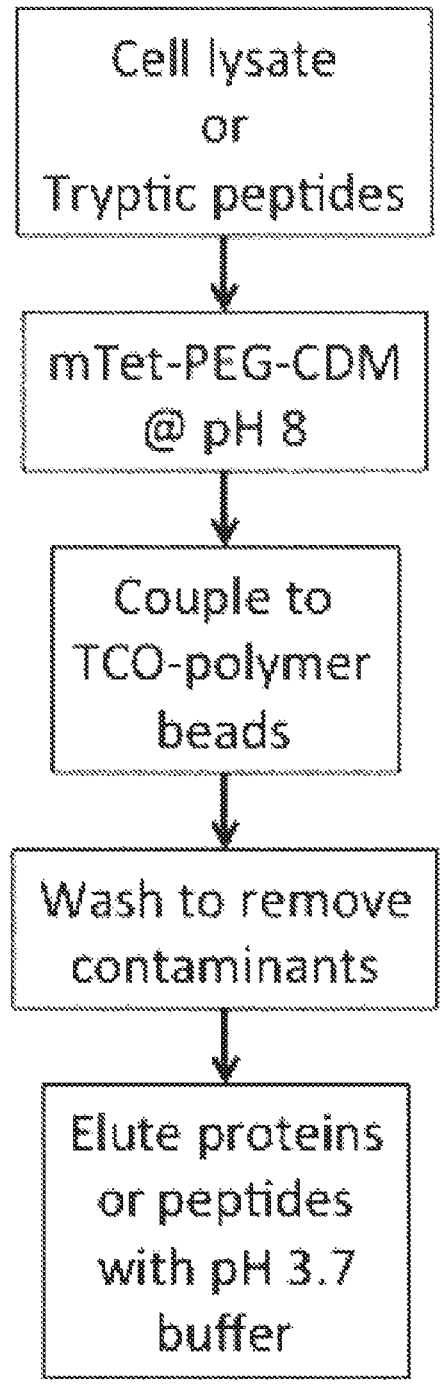
FIG. 5 illustrates an exemplary protein purification workflow as described in Example 1.

Cell lysate is prepared by a variety of methods, such as lysis by SDS, urea, or RIPA buffer. If intact protein proteomes are desired, the proteins in the cell lysate are coupled to mTet-CDM under mildly basic conditions, pH 8-9.5. If peptides are desired, the proteins in the lysate are digested by proteolytic enzymes, such as trypsin or Lys C, for example and without limitation trypsin comprising biotin and tetrazinyl pendant moieties, such as MB-trypsin described below. Where tetrazinyl-modified trypsin is used, the trypsin is removed after digestion by coupling of the tetrazinyl-modified trypsin to substrate-bound TCO, e.g., bead-bound TCO. Other bio-orthogonal reaction chemistries, such as IEDDA coupling pairs, may be used to decorate the trypsin and remove the trypsin from the digested protein mixture. The resulting peptide fragments are then coupled to mTet-CDM under mildly basic conditions, e.g., pH 8-9.5. For either intact proteins or peptides, an aliquot of TCO beads sufficient to bind the total amount of mTet-CDM in the sample prep reaction is added to the sample. The samples are then incubated (0° C.-37° C.) with shaking to allow the mTet:TCO click reaction to occur. This is expected to require 1-10 hours, until no free mTet is detected. The beads are then washed repeatedly (3-5 times) to remove non-protein contaminants. A variety of wash buffers may be used to ensure the complete removal on non-protein substances. These buffers may include SDS, urea or salt. The proteins/peptides bound to the beads are then eluted under mildly acidic (e.g., pH 2.5-6) conditions to reverse the CDM-protein/peptide linkage. The reversal buffers also contain components suitable to downstream workflows. This may include urea, SDS, detergents, salts or organic solvents. This yields a purified protein or peptide sample free of contaminants. FIG. 5 shows the workflow.

Figure 6:
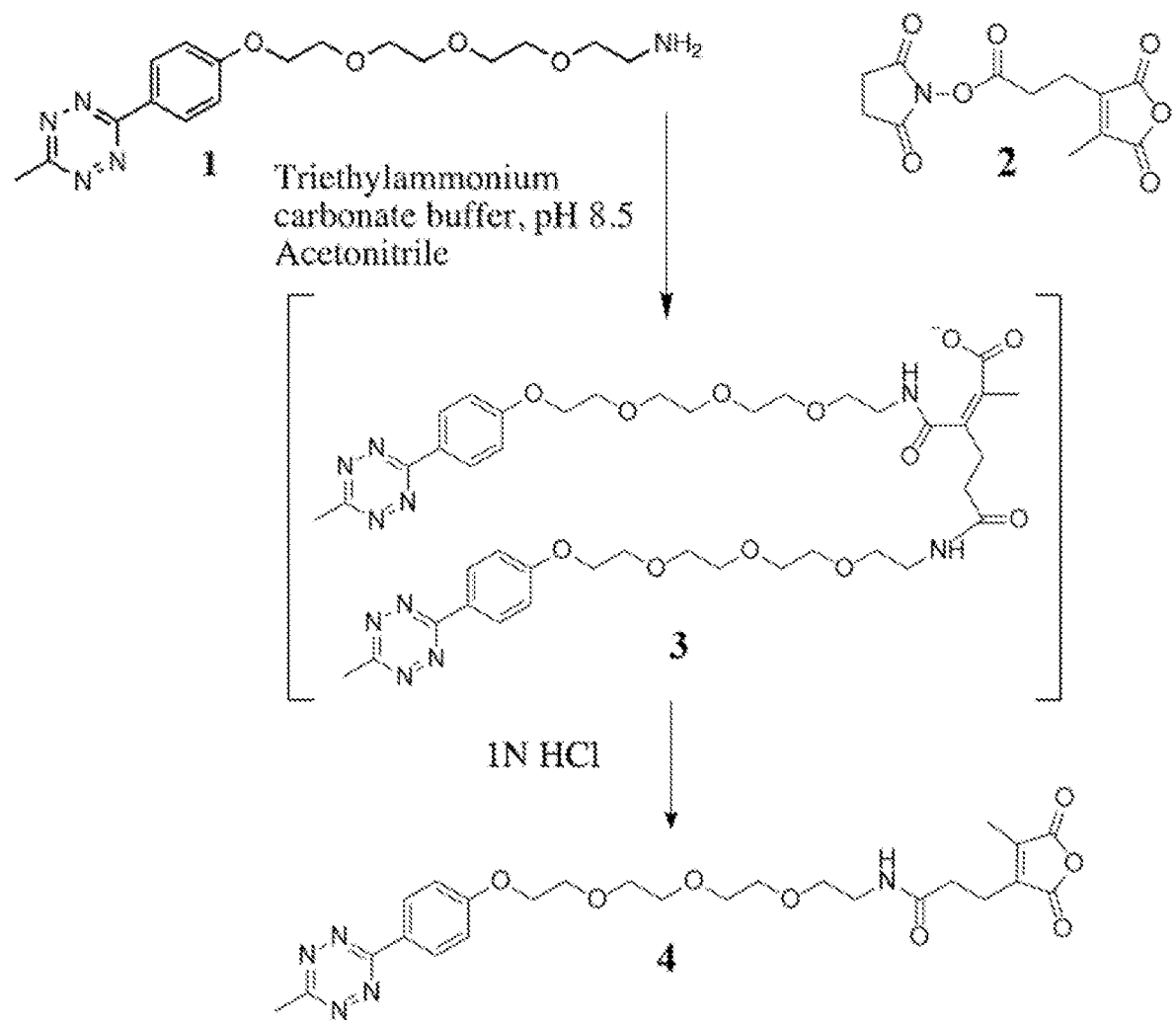
FIG. 6 shows a synthesis scheme of mTet-PEG$_4$-CDM.

FIG. 6 shows the synthesis scheme for of mTet-PEG-CDM. The starting materials are mTet-PEG4-amine (compound 1) and 2-carboxyethyl-3-methyl-maleic anhydride N-hydroxysuccinimidyl ester (CDM-NHS) (compound 2) (custom synthesized). Because CDM-NHS has two amine-reactive moieties, two moles of mTet-PEG-amine is combined with one mole of CDM-NHS giving an intermediate product 3. Because the linkage between CDM and mTet-PEG-amine is acid-labile, treatment with HCl reverses that linkage and forms the activated CDM anhydride of mTet-PEG-CDM 4. The final product is purified by liquid chromatography and analyzed by NMR and MS.

A non-limiting example synthesis of mTet-CDM is as follows: mTet-PEG4-NH2 hydrochloride 1 (5 mmol) was dissolved in 1M triethylammonium bicarbonate buffer pH 8.5 (10 ml). CDM-NHS ester 2 (2.5 mmol) dissolved in dry acetonitrile (ACN, 5 ml) was added dropwise under stirring at room temperature. Stirring was continued for 1 h. The reaction mixture was concentrated to a volume of 1 ml. 2N HCl (5 ml) was added to hydrolyze 3 and the reaction mixture was stirred for 30 min. The reaction mixture was separated by MPLC chromatography on a SEPACORE® system on RP-18 with acetonitrile/water/0.1% TFA as mobile phase using a step-gradient. The product eluted at about 20% acetonitrile (monitoring at 254 nm). The product fractions were analyzed by UPLC (Waters), RP-18 column, acetonitrile/water/0.1% TFA, 0-0.5 min, 0% acetonitrile, 0.5 min-3 min 0-100% acetonitrile linear gradient, run time 5 min, monitoring at 240 nm and 256 nm. Pure fractions were collected and concentrated to yield 486 mg (34%) of the pink resinous product 4.

Synthesis of TCO Beads

Figure 7:
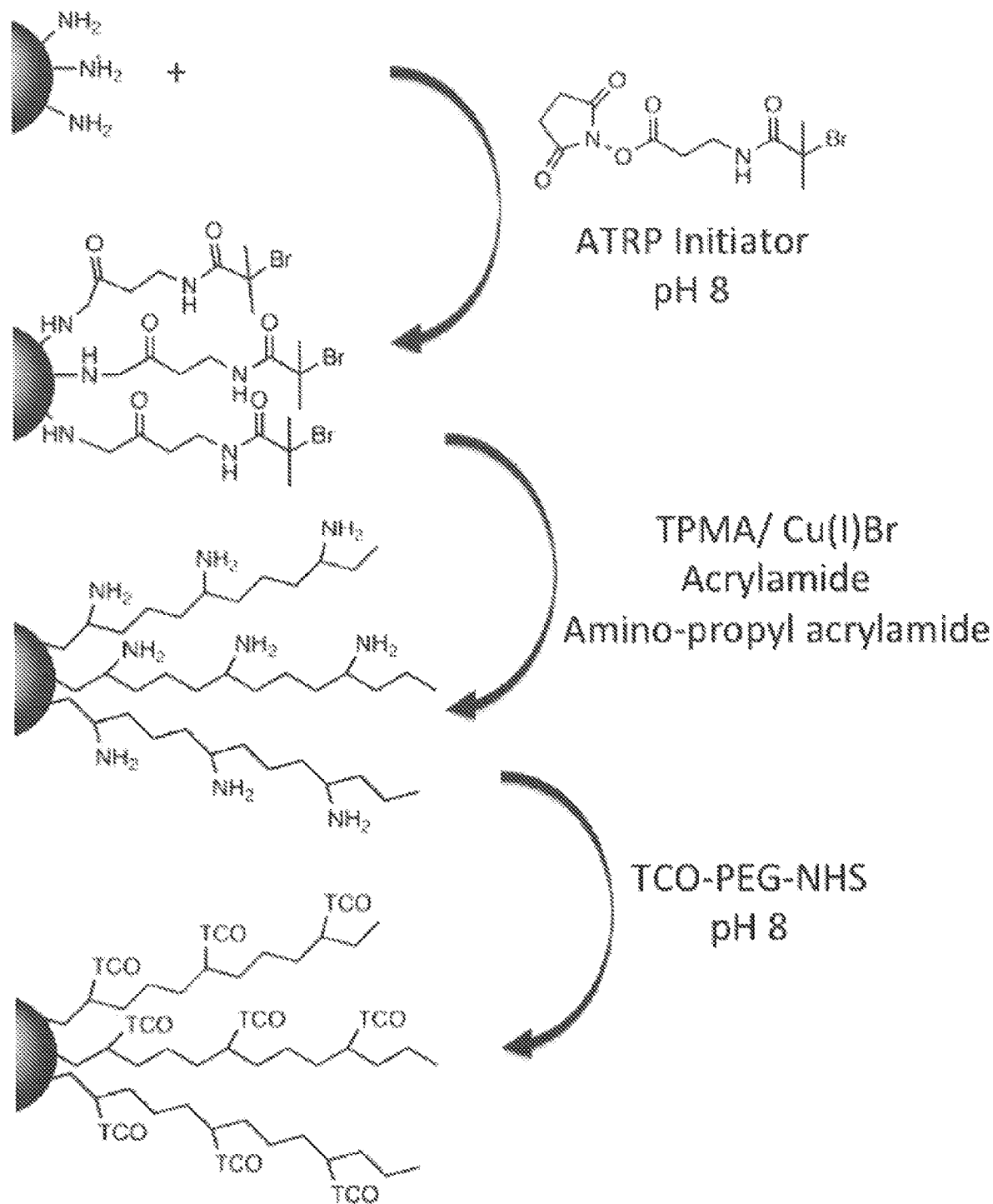
FIG. 7 provides an illustrative synthesis scheme for TCO beads.

As an example of a substrate for binding the proteins or protein fragments for protein isolation, TCO beads are made by growing high density of polymer chains from the surface of the amine beads using ATRP. The first step in the process is to couple the initiator molecule to the amine beads (FIG. 7). The initiator, N-2-Bromo-2-methylpropanoyl-NHS ester, is coupled using standard NHS ester coupling conditions. The concentration of initiator is adjusted to achieve near complete coupling. A copolymer of acrylamide and aminopropyl acrylamide is grown from the surface of the initiator-bound beads. The goal is to increase the amine content of the beads 10-fold to 50-fold. The ratio of acrylamide and aminoethyl acrylamide and the length of the copolymer is adjusted to maximize amine content without significantly increasing viscosity or accessibility of proteins/peptides to the inner reaches of the polymer coat. Acrylamide is included in the copolymer to avoid overly dense packing of aminopropyl sidechains. The final step in the synthesis is coupling TCO-PEG-NHS to the aminoethyl sidechains. The concentration of TCO-PEG-NHS will be adjusted to maximize coupling. Any un-coupled amine will be blocked by acetic anhydride to prevent non-specific protein binding. Polyacrylamide and PEG are well-known for their low levels of non-specific protein binding.

Example 2—Preparation and Characterization of MB-Trypsin

Methyltetrazine-biotin-trypsin (MB-Trypsin) was prepared by combining: 1 ml of 1 mg/ml Trypsin in 25 mM HEPES-NaOH pH 8.0, 10 mM $CaCl_2$, 3 mM benzamidine HCl, 140 µl of 100 mM Biotin-NHS in dry DMF; and 28 µl of 100 mM methyltetrazine-PEG4-NHS in dry DMF. The mixture was incubated for 30 minutes at 0° C. and dialyzed overnight versus 2×1 L of 25 mM HEPES-NaOH pH 8.0, 10 mM CaCl2. The M-trypsin may be stored at 4° C. for up to 60 days with <10% loss of activity, or −80° C. for longer periods of time.

The MB-trypsin may be characterized by the following assay. Combine 1 ml Reaction buffer (46 mM HEPES-NaOH pH 8.0, 11.5 mM $CaCl_2$, 1 mM tosyl-arginine methyl ester (TAME)) with 1 µl~1 mg/ml trypsin solution. Measure rate of light absorption at 247 nm and calculate nmoles of TAME hydrolyzed per minute per µg trypsin. Labeling of trypsin with methyltetrazine and biotin does not reduce trypsin's catalytic activity.

A fluorescamine assay may be used to assess the extent of primary amine labeling according to the following. Make standard curve by dissolving 0-10 µg of trypsin or 10 µg of MB-Trypsin in 200 µl of 100 mM HEPES-NaOH pH 8.0. Add 50 µl 3 mg/ml fluorescamine in acetone. Mix and transfer 200 µl of each reaction to a black, 96-well plate for fluorescence measurement in a plate reader. Measure fluorescence using an excitation wavelength of 390±5 nm and an emission wavelength of 465±10 nm. Calculate extent of free amines in MB-Trypsin sample relative to the standard curve. Typically, >95% of the amines are labeled under the above labeling reaction conditions.

Trypsin protein digestion protocol: Combine equal amounts of MB-Trypsin with target protein(s) [typically, 100 µg of MB-Trypsin and 100 µg target protein in a total volume of 400 µl] in buffer containing 100 mM HEPES-NaOH pH 8.0 and a denaturant cocktail with 1% sodium dodecylsulfate (SDS), 1% IGEPAL® and 0.5% sodium deoxycholate. The target protein(s) are previously reduced with dithiothreitol and alkylated with iodoacetamide. Digestion is typically complete within 2 hours at 37° C.

MB-Trypsin stability: MB-trypsin is fully active in buffer containing up to 0.1% SDS, in buffer containing up to 4 M urea, and after up to 3 freeze-thaw cycles at −80° C.

Example 3

Labeling of proteins and peptides with mTet-CDM. Labeling of proteins or peptides with mTet-CDM was performed under two different buffering conditions. Briefly, protein at a concentration of 0.5 mg/mL in 100 mM HEPES, pH 8.0 and 25 mM NaCl was incubated with mTet-CDM (30 mg/mL in ACN) at a 1-6 mass fold excess of mTet-CDM over protein. Labeling was reported as $$\frac{gmTet - CDM}{g\ protein}.$$

The mTet-CDM was always added at a volume less than 10% the total volume of the reaction. The reaction was incubated for 1 hour at 4° C. This labeling procedure was also repeated in a buffer containing 10 mM HEPES, pH 8.0 and 25 mM NaCl.

The extent of mTet labeling was determined using a fluorescamine assay for the detection of free primary amines. A standard curve of the unlabeled sample was made using 0-10 µg of unlabeled protein/proteome/peptide. Each standard was diluted to a final volume of 250 µL of 10 mM HEPES, pH 8.0. Fluorescamine was dissolved in acetone at a concentration of 3 mg/mL and 50 µL of this solution was added to each solution and mixed well. This was repeated for the mTet labeled sample. The solutions were transferred to a black polystyrene flat bottom Greiner CELLSTAR® 96 well plate from MilliporeSigme (St. Louis, Mo.). Fluorescence was determined using a Tecan Spark® microplate reader from Tecan Group Ltd. (Switzerland). Excitation was performed using excitation at 400 nm, 30 nm bandwidth and emission detection at 460 nm, 40 nm bandwidth. A standard curve was created by plotting fluorescence intensities vs. free amines, and the number of free amines in the mTet sample was found by solving for free amines using the fluorescence intensity value and the standard curve equation.

Binding of mTet labeled proteins to TCO conjugated beads. TCO agarose beads were purchased from Click Chemistry Tools (Scottsdale, Ariz.). To test buffer conditions for prevention of non-specific binding, two stock solutions of unlabeled and 6× mTet-CDM labeled, Cy5 labeled carbonic anhydrase were made as described previously with the following change. After addition of mTet-CDM, samples were incubated 15 min at room temperature before addition of 0.83 nmols of Cy5-NHS, followed by an incubation for 1 hour at 4° C. In separate tubes, 0.15 µg of unlabeled or 6× mTet labeled carbonic anhydrase (mTet-CA) was added to 100 µL of each of the following buffers: (A) 0.3 M NaCl and 100 mM HEPES, pH 8.0, (B) 1% SDS and 100 mM HEPES, pH 8.0, (C) 0.3 M NaCl, 1% SDS, and 100 mM HEPES, pH 8.0. To each buffer solution, 50 µL of TCO beads equilibrated in the same buffer was added and incubated for 1 hour at room temperature with end over end rotation. A loading control for each sample was made by incubating the corresponding carbonic anhydrase in the corresponding buffer without the addition of TCO beads. Binding was assessed by running the supernatant of each sample and load control on a 4-20% SDS-PAGE gel for 1 hour at 130 V. Images were acquired using an in-house built imager. The amount of labeled or unlabeled carbonic anhydrase remaining unbound was quantified via pixel density of the fluorescence images using ImageJ. The load samples containing only the corresponding amount of labeled or unlabeled carbonic anhydrase were used as a baseline. All other carbonic anhydrase amounts were calculated as a percentage of the load. The amount bound to the TCO beads was calculated by subtracting the amount of carbonic anhydrase remaining free in solution from 100%.

To test the amount of time needed for complete binding of mTet labeled protein to the TCO beads, a time course for binding was performed. TCO beads were equilibrated in 1% SDS, 0.3 M NaCl, 100 mM HEPES, pH 8.0 and 30 µL of the equilibrated beads were incubated with 25 µg of 6× mTet-CA with a final total volume of 80 µL. Reactions were incubated at 4° C. with 1400 rpm shaking for 0 min, 5 min, 15 min, 30 min, or 60 min. After the designated incubation time, beads were spun down to a pellet and the supernatant was removed. A loading control was made by suspending the same amount of 6× mTet-CA in the same amount of buffer in the absence of TCO beads. Binding was assessed by running the supernatant of each sample and load control on a 4-20% SDS-PAGE gel for 1 hour at 130 V. Images were acquired using an in-house built imager. The amount of mTet-CA carbonic anhydrase remaining unbound was quantified via pixel density of the fluorescence images using ImageJ. The load samples containing only the corresponding amount of mTet-CA was used as a baseline. All other mTet-CA amounts were calculated as a percentage of the load. The amount bound to the TCO beads was calculated by subtracting the amount of mTet-CA remaining free in solution from 100%.

Elution of mTet labeled protein from TCO beads. Elution of mTet labeled protein from TCO beads was done using elution buffer for two-dimensional difference gel electrophoresis (2D-DIGE) (20 mM citrate, pH 3.0, 7 M urea, 2 M thiourea, 10 mM DTT, 4% CHAPS). mTet-CA was bound to beads as previously described and washed 3× with 100 µL of binding buffer containing 10 mM HEPES, pH 8.0 instead of 100 mM HEPES, pH 8.0. Lowering the HEPES buffer concentration in the wash helps with the elution step. Protein was eluted from the beads by incubating with 50 µL of elution buffer with 1400 rpm shaking at room temperature. The supernatant was transferred to a fresh tube and the elution step was repeated three more times. Elution incubation times were performed at 15 min, 30 min, 60 min, and 120 min. Elution yields from the beads were assessed for each incubation time and each individual wash was also analyzed for protein elution. A loading control for each sample was made by incubating the starting amount of mTet-CA in elution buffer. The percent of CA released was assessed using SDS-PAGE and image analysis as previously stated. All other carbonic anhydrase amounts were calculated as a percentage of the load to get the percent yield. For each individual wash, pixel counts were added together to get the total pixels for carbonic anhydrase over the whole elution. Then, each lane pixel density was calculated as a percentage of the total to determine how much protein was eluted in each wash step.

Capture, wash, and release of whole yeast proteomes using 1D and 2D gel electrophoresis. Yeast lysates were made using strain JWY6147 leu2 his3 trp1 ura3 provided by John Woolford's lab at Carnegie Mellon University. Pelleted yeast cells were resuspended in lysis buffer for 2D-DIGE and glass beads were added to equal half of the total volume. Cells were lysed by vortex six times with the glass beads in 30 s intervals with 30 s on ice in between each interval. After lysis, cellular debris was pelleted by centrifugation at 7,000 rpm for 10 min and the supernatant was transferred to a fresh tube. Protein concentration was found using the standard Bradford assay.

After quantification, the proteome was 6× labeled with mTet-CDM and labeled with Cy5 as previously described. In a LoBind Eppendorf tube, 200 µL of TCO beads were washed 3× with 200 µL of lysis buffer. Next, 100 µg of 6× mTet labeled proteome was added to the beads and incubated for 1 hour at room temperature with 1400 rpm shaking. The supernatant was removed and discarded and the beads washed 3× with 200 µL lysis buffer. After washing, proteins were eluted from the beads by adding 50 µL of 2D-DIGE elution buffer and incubating 30 min with 1400 rpm mixing. After elution, the supernatant was removed and transferred to a fresh tube. This was repeated twice. After pooling all the elutions together, yields were first tested by running the sample on a 4-20% SDS-PAGE gel for 1 hour at 130 V. The elutions were run with a load sample containing the starting amount of proteome used in this experiment in elution buffer. Yields were quantified as described previously.

For 2D-DIGE analysis of the eluted proteome, 20 µg of unlabeled proteome was labeled with Cy3 in 2D-DIGE lysis buffer as previously described for use as a control. After labeling, 57 µL of the control sample was combined with 57 µL of the elution sample. To this sample, 2.4 µL of 3-10 NL IPG buffer (GE Healthcare Bio-Sciences, Pittsburgh, Pa.) was added and the samples were run using 2D-DIGE. IPG strips (18 cm, pH 3-10 NL) were purchase from GE Healthcare Bio-Sciences (Pittsburgh, Pa.) and rehydrated for 16 hour with a rehydration buffer containing 0.2% 3-10 NL IPG buffer. Isoelectric focusing (IEF) was performed using a Protean IEF instrument purchased from Bio-Rad (Hercules, Calif.). Equilibration was done using an in gel method described previously. The second dimension SDS-PAGE was performed using a 12% resolving gel on a Protein II xi electrophoresis apparatus purchased from Bio-Rad (Hercules, Calif.). Images of the gel were acquired using an in-house built imager. ImageJ was used to create the comparative stack. First, guide stars on the gel were used to set the brightness and contrast to comparative levels. Then, the color of each gel was changed using the lookup table function. Cy3 for the control was set to green, while Cy5 for the elution was set to red. Each image type was then changed to RGB color and the paste control set to add. From there, all of the control image was selected and added to the elution image.

Figure 8:
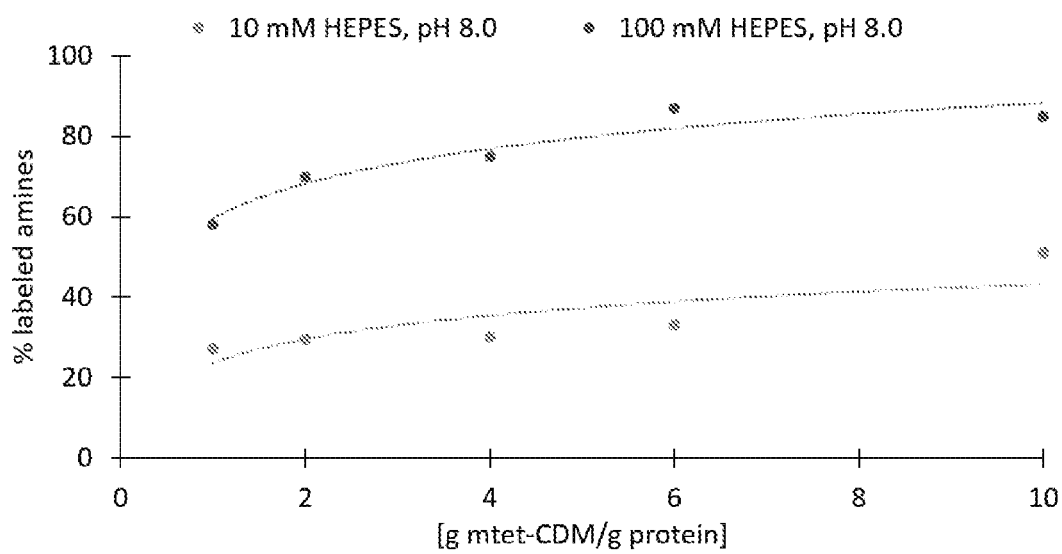
FIG. 8 Labeling of primary amines with mTet-CDM is more efficient in 100 mM HEPES and plateaus at ~80% labeling for carbonic anhydrase. Carbonic anhydrase protein was labeled with mTet-CDM in the presence of 10 mM HEPES pH 8.0 (shown in light blue) or 100 mM HEPES, pH 8.0 (shown in dark blue). While labeling in 10 mM HEPES, pH 8.0 plateaued at ~30% labeling, labeling in 100 mM HEPES, pH 8.0 plateaued at ~80%, showing that higher concentrations of HEPES are important for extensive labeling FIG. 9. Buffer containing 0.3 M NaCl and 1% SDS performed the best for preventing non-specific binding of protein to TCO beads.

Labeling of single proteins with mTet-CDM. After purification of mTet-CDM, we next wanted to know how much mTet-CDM is needed to efficiently label primary amines on proteins. We labeled the protein carbonic anhydrase with mTet-CDM in the presence of 10 mM HEPES, pH 8.0 or 100 mM HEPES, pH 8.0 and analyzed the extent of labeling using a fluorescamine assay. Labeling was much more efficient in 100 mM HEPES, pH 8.0 than in 10 mM HEPES, pH 8.0 (FIG. 8). While labeling in 10 mM HEPES, pH 8.0 plateaued at ~30%, labeling in 100 mM HEPES, pH 8.0 plateaued at ~80%. The higher concentration of HEPES likely helps stabilize the slightly basic pH, ensuring the proper protonation state of the primary amine needed on the protein and opening of the maleic anhydride ring. The need for higher concentrations of HEPES had also been demonstrated by previous students working with biotin-CDM. Based on this, all labeling in this study was done using 6× labeling in 100 mM HEPES, pH 8.0.

Figure 9:
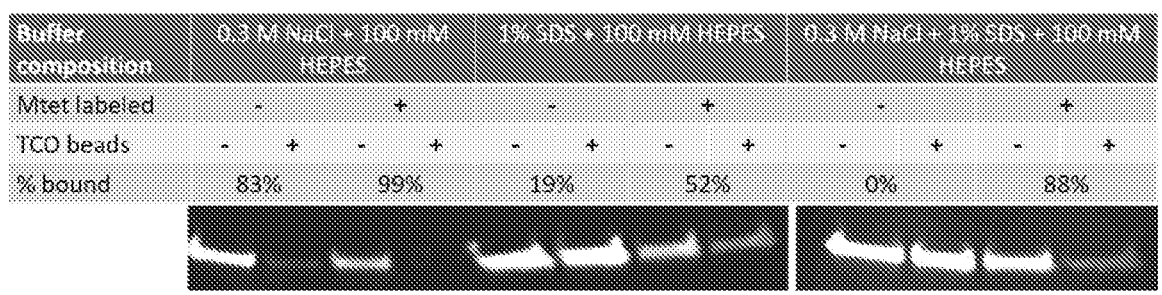

Optimizing buffer conditions and incubation times for binding of mTet labeled proteins to TCO beads. To optimize conditions for binding of mTet labeled proteins to TCO beads, we first wanted to establish the proper buffer conditions necessary for preventing non-specific binding. We knew from previous experience with avidin beads that proteins tend to stick to beads non-specifically, leading to lower protein yields. We also knew that high SDS and high salt present in the buffer could help prevent non-specific binding. To find the buffer condition that would prevent non-specific binding to TCO beads, we incubated both mTet labeled and unlabeled carbonic anhydrase with TCO beads in the presence of 0.3 M NaCl, 1% SDS, or both together. We found that 0.3 M NaCl alone does not prevent non-specific binding of unlabeled protein to the beads, with loss of 83% of the unlabeled protein on the beads (FIG. 9). Surprisingly, while 1% SDS alone does prevent non-specific binding, it also greatly reduced binding of mTet labeled protein to the TCO beads, with only 52% binding. Buffer containing both 0.3 M NaCl and 1% SDS showed the best results with no detectable non-specific binding and high binding of labeled protein to the TCO beads at 88%. This agrees with previous work using biotin-CDM and avidin beads where the buffer containing both 0.3 M NaCl+1% SDS also gave the best results. For all future assays in this chapter, the buffer for binding to TCO beads contained 0.3 M NaCl, 1% SDS, and 100 mM HEPES, pH 8.0 was used.

To determine optimal buffer conditions for preventing non-specific binding to TCO beads, mTet labeled or unlabeled carbonic anhydrase was incubated with TCO beads in different binding buffers. The protein that is not mTet labeled represents any binding via nonspecific interactions, while the mTet labeled sample represents binding via specific interactions. The samples lacking TCO beads are the load used to calculate the % bound to the TCO beads. The buffer containing 0.3 M NaCl and 1% SDS performed the best at preventing non-specific binding of unlabeled carbonic anhydrase to the TCO beads while still allowing binding of mTet labeled carbonic anhydrase to the TCO beads.

Figure 10:
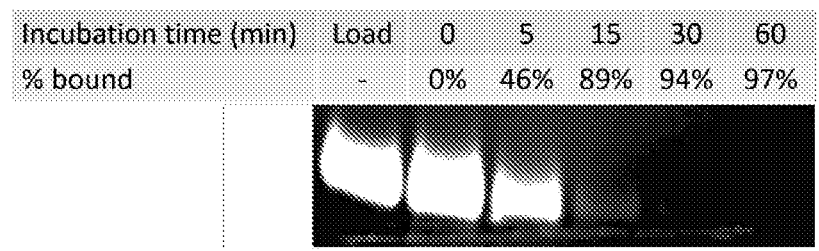
FIG. 10. Binding of mTet-CA to TCO beads reached 94% in 30 min. To figure out optimal incubation times for binding of mTet labeled protein to TCO beads, a time course was performed over 1 hour and binding of mTet-CA to TCO beads was assayed. After 30 min, 94% of mTet-CA was bound to the TCO beads and plateaued after this time point. For all future binding events, the 30 min incubation time was used.
Figure 10:
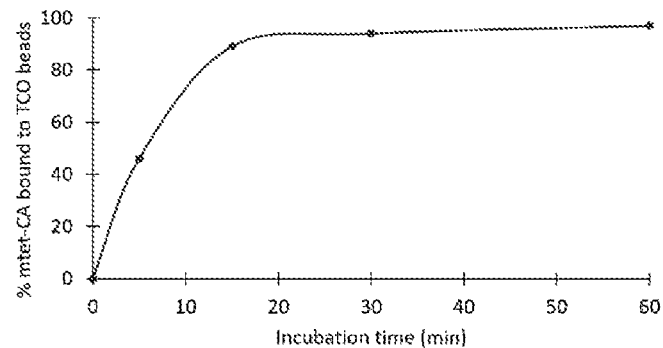

We next tested for the incubation time required for complete binding of mTet labeled protein to TCO beads. A time course was performed using a set amount of mTet-CA and TCO beads, with binding being assayed over the course of 1 h. After just 30 min, 94% of mTet-CA was bound to the TCO beads (FIG. 10). Binding showed little change after this time point, increasing 3% after 1 hour to reach 97% binding. Based on this time course, all future binding of mTet labeled protein was performed using a 30 min incubation time.

Figure 11:
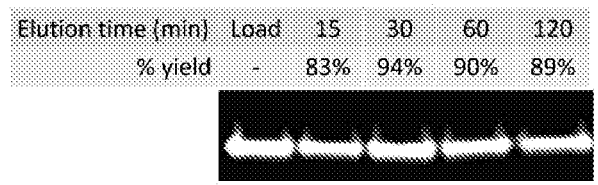
FIG. 11. mTet-CA was eluted from TCO beads in three washes with incubation times as little as 15 min. mTet-CA bound to TCO beads was eluted in four washes with increasing incubation times. Total elution yields for each incubation time (A) and elution yields of each individual wash (15 min incubation elution used as a representative figure B) were calculated and compared. All elution incubation times gave yields higher than 80%, with 30 min giving the highest yield at 94%, and 89% of the eluted protein is found in the first two elution washes.
Figure 11:
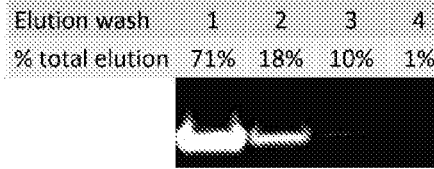

Optimization of elution incubation time and wash number. To optimize elution of proteins from the TCO beads, two factors were considered: incubation time in elution buffer, and the number of washes in elution buffer required for complete removal from the beads. Because there is a certain amount of dead volume in the agarose beads, proteins cannot be removed in only one elution step by removing the supernatant after incubation in elution buffer. Rather, the beads must be incubated in elution buffer and then the protein collected in multiple washes of the beads to ensure no protein is lost in the dead volume of the beads. However, each wash in elution buffer will dilute the final protein concentration and too much dilution is undesirable for proteomic techniques like 2D-DIGE and MS, especially if low abundance proteins are the desired target. Finding the right balance between incubation time and number of washes was important to ensure fast, concentrated elution of protein from the TCO beads.

mTet-CA was bound to TCO beads and then eluted from the beads using four washes with increasing incubation times. Yields for each incubation time were calculated and compared. All elution times showed yields greater than 80%, with the highest yield (94%) at 30 min (FIG. 11 (A)). This agrees with previous work that showed that dimethyl maleic anhydrides recyclize in as little as five minutes. Individual washes were analyzed for protein elution to determine the point at which all protein had eluted from the beads. More than 85% of the eluted protein comes off the beads in the first two washes, and three washes gives 99% of all eluted proteins (FIG. 11 (B)). Based on these results, elution for the rest of this study was done using three washes with 30 min incubations each.

Capture, wash, and release of whole yeast proteomes using mTet-CDM and TCO beads.

Figure 12:
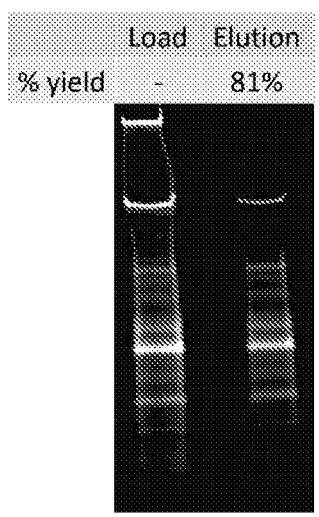
FIG. 12. Capture, wash, and release of whole yeast lysates resulted in yields of 81%. A sample containing 100 μg of yeast proteome was labeled with mTet-CDM and cleaned up using our capture, wash, and release sample preparation workflow. After elution, over 80% of the proteome was recovered.

With capture and release of single proteins giving yields higher than 90%, we next sought to apply this technology to capture, wash, and release the entire proteome. Yeast cells were lysed and cellular debris removed from solution. The proteome was 6× labeled with mTet-CDM and captured, washed, and released using the previously established parameters. Elutions were then run on an SDS-PAGE gels for quantification. After the entire sample preparation workflow using mTet-CDM and TCO beads, over 80% of the proteome was recovered (FIG. 12). This yield is much higher than sample preparation methods used in the field today, showing promise for this technique in proteome sample preparation. However, this yield is lower than what was observed for single proteins and could be due to interfering molecules present in the lysate. More work will need to be done to optimize this workflow for whole proteome purification.

Figure 13:
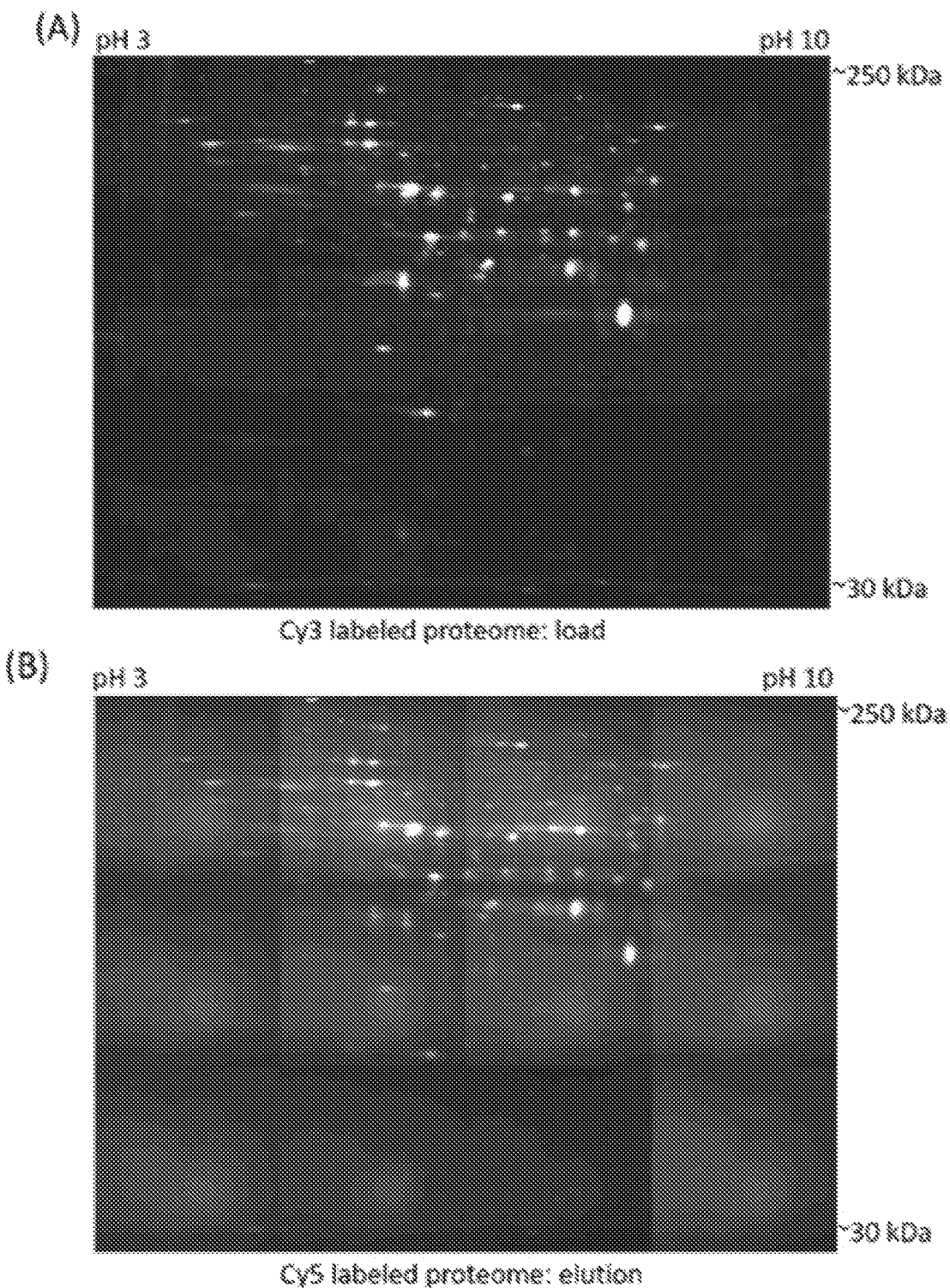
FIG. 13. 2D-DIGE of eluted proteins show similar proteome profiles, with a few spots more enriched in the load or elution sample. A yeast proteome sample that did not go through the proteome sample preparation workflow (A) and a yeast proteome sample that did go through the proteome sample preparation workflow (B) were compared using 2D-DIGE.

The eluted yeast proteomes were also analyzed using 2D-DIGE. While 2D-DIGE can't be used for quantification, it can show specific protein loss, and will make any systemic bias for our sample preparation method obvious. The eluted proteins were labeled with Cy5 dye and a load control was labeled with Cy3 dye. These samples were combined and then separated by their isoelectric points and their molecular weights. The gel was then imaged using filters for both Cy3 and Cy5. The two images were overlayed to show any protein loss between the two samples. If there was biased protein loss during the workflow, there would be specific spots that show up only in the Cy3 load sample and not the eluted Cy5 sample. After comparison of the load and elution proteomes, it was observed that most proteins overlay very well with one another (FIG. 13). It should be noted that the eluted proteome was labeled first with mTet-CDM, which takes up the same primary amines used for attachment of the Cy dyes. That means that the labeling with the Cy5 dye is much dimmer than for the load control used for comparison, which can make it appear as if there are spots in the load that are not in the elution, when they simply aren't visible. While these results are promising, dye labeling using thiol groups instead of using primary amines would prevent the discrepancy in brightness of the spots between the load and elution, allowing for quantification. Future experiments should explore alternative methods for dye labeling or comparing separate gels using silver stain, as well as using reciprocal labeling if still using dye labeling to ensure no dye dependent changes are being observed.

Example 4

*Burkholderia cenocepacia* lysate clean up using spin column.

A pellet of *B. cenocepacia* culture bacteria was lysed by boiling for 5 minutes in a solution of 100 mM HEPES pH 8.0, 2% SDS. The viscous solution was briefly sonicated with a probe Sonicator for about 15 seconds at 30% power. The resulting bacterial cell lysate had a concentration of 120 mg/ml. The reaction was conducted for 1 hour at room temperature (RT) with a mixture of 153.3 µl $H_2O$, 20 µl 1M HEPES pH 8; 10 µl 10 mg/ml *B. cenocepacia* lysate, and 16.7 µl 30 mg/ml mTet-CDM. 150 µl of TCO beads (purchased from Click Chemistry Tools (Scottsdale, Ariz.)) were washed 3× in 500 µl of 100 mM HEPES pH 8+10% ACN.

The sample was processed according to the following:

1. Remove 20 µl of reaction for loading control

2. Add 180 µl of reaction to beads in cold room—Mix end-over-end for 1 hour (note: the solution went from pink to colorless in ~15 minutes)

Figure 14:
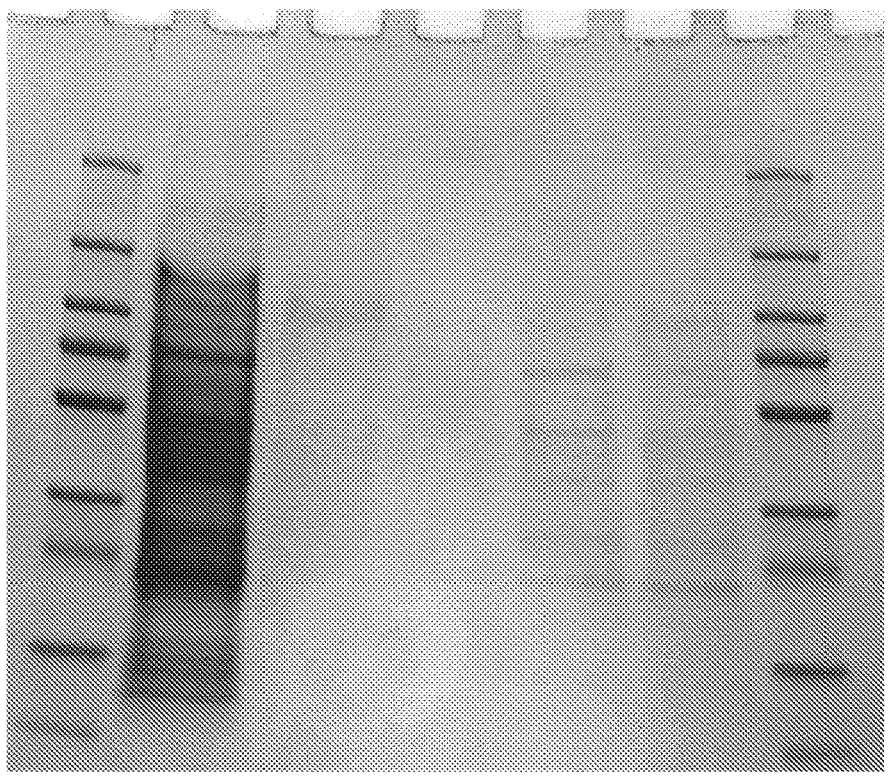
FIG. 14. Assessment of whole protein cleanup workflow. Lane 1: Load, Lane 2: Unbound, Lane 3: Elution 1, Lane 4: Elution 2, Lane 5: Mock Elution. Note the urea in the eluted fractions reduces the Coomassie Blue staining of the protein samples. Lane 5 shows the same amount of protein in the load sample, but in the elution buffer. This reveals that nearly 100% of the loaded protein was eluted.
Figure 15:
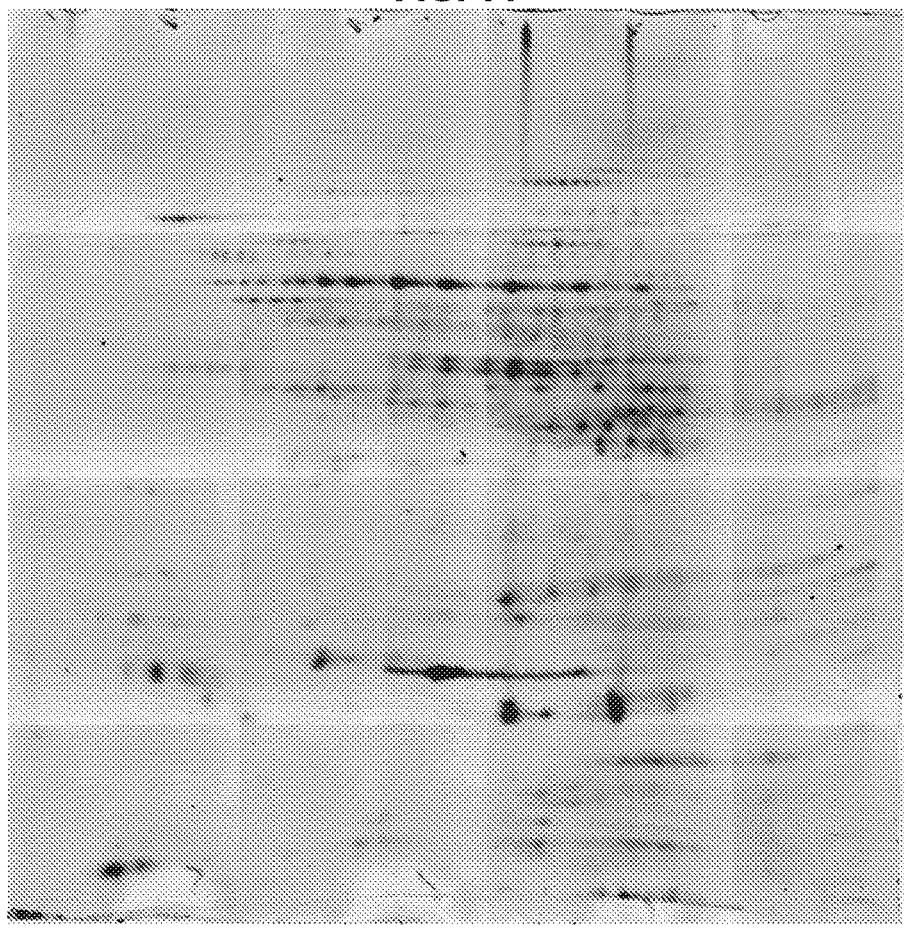
FIG. 15. Two dimensional electrophoresis gel of Cy3-*Burkholderia* lysate after cleanup.

3. Wash the beads 3×400 μl WB [7M urea, 2M thiourea, 4% CHAPS, 10 mM DTT]+1 mM HEPES pH 8
4. Elute 2×50 μl WB+5 mM Formic acid
5. Run 10% of each step on SDS-PAGE. Make mock eluate with lysate in WB+5 mM Formic acid
6. Combine eluates and run, make basic with 10 mM TEAB, label with Cy3-NHS and run on 2DE gel and two-dimensional electrophoresis gels (FIGS. 14 and 15).

Example 5

The following evaluates how much labeling is necessary for close to 100% recovery of a peptide mixture containing alcohol dehydrogenase, carbonic anhydrase lysozyme, and bovine serum albumin. Table A provides the reaction mixtures tested (μl).

TABLE A

|  | 0× | 21× | 45× | 75× | 100× |
|---|---|---|---|---|---|
| 0.25 mg/mL peptide* | 20 | 20 | 20 | 20 | 20 |
| H₂O | 19.7 | 19.7 | 19.7 | 19.7 | 19.7 |
| 1M HEPES | 7.0 | 7.0 | 7.0 | 7.0 | 7.0 |
| 90% ACN | 23.3 | 19.8 | 15.8 | 10.8 | 6.6 |
| 30 mg/mL mtTet-CDM | 0 | 3.5 | 7.5 | 12.5 | 16.7 |
| Total | 70 | 70 | 70 | 70 | 70 |

Figure 16:
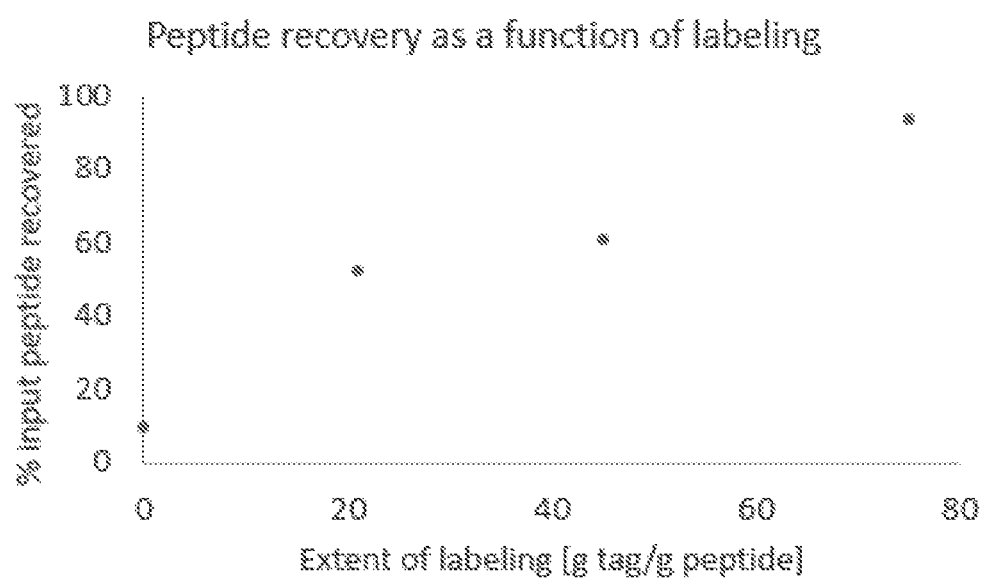
FIG. 16 provides a graph showing the recovery of the peptide of Example 5, relative to the amount of mTet-CDM conjugated to the peptide.

The samples were processed as follows:
Set up labeling reactions above, incubated at room temp for 1 hour.
During incubation, washed 225 μl of TCO beads per reaction 3× with 400 μl 100 mM
HEPES pH 8.0, 0.2% SDS.
Washed beads in the column frits.
Completely dried the beads before adding the diluted labeling reactions.
Brought labeling reaction volume to 500 μl with 100 mM HEPES pH 8.0, 0.2% SDS.
Added diluted labeling reaction to washed TCO beads in column frits with end caps on.
Taped columns into Eppendorf tubes to serve as adapters for the rotisserie.
Incubated in the cold room on a rotisserie for 1 hour.
Recovered the supernatant.
Washed beads 2 times with 10 mM HEPES pH 8.0, 25% ACN.
Washed beads 2 times with water.
Added 120 μl 0.1% formic acid and incubated with agitation (1500 RPM) at 8° C. (set block to 4° C., only got to 7° C.) for 1.5 hours.
Recovered eluate.
Added 120 μl 0.1% formic acid 50% ACN and incubated with agitation (1500 RPM) at 7° C. for 1.5 hours.
Recovered eluate.
Added 120 μl 0.1% formic acid 50% ACN and incubated with agitation (1500 RPM) at 7° C. for 1 hour.
Recovered eluate.
Set up four standard curves—matching to the various buffers in the samples.
Input standard curve: 100 mM HEPES pH 8.0, 30% ACN.
Supernatant standard curve: 100 mM HEPES pH 8.0, 1.35% SDS
Elution 1 standard curve: 0.1% FA
Elution 2,3 standard curve: 0.1% FA, 50% ACN
Prepared samples for fluorescamine assay as follows:
Input: 17.5 μl of 70 μl labeling reaction+182.5 μl 100 mM HEPES pH 8.0.
Supernatant: 125 μl of 500 μl supernatant+75 μl 100 mM HEPES pH 8.0.
Elutions: 30 μl of 120 μl eluate+170 μl 100 mM HEPES pH 8.0.
Added 50 μl 3 mg/ml fluorescamine dissolved in acetone to each sample, mixed well, and aliquoted 200 μl into a 96 well plate.
Results (Table B, FIG. 16)

TABLE B

|  | Input | Elution total | % of input |
|---|---|---|---|
| 0× | 26.52 | 2.60 | 9.81 |
| 21× |  | 13.81 | 52.06 |
| 45× |  | 16.03 | 60.47 |
| 75× |  | 24.79 | 93.48 |

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A coupling compound having the structure:

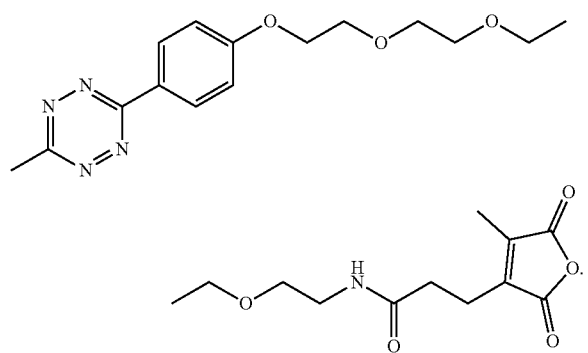

2. A method of purifying a polypeptide, comprising:
   mixing a sample having a basic pH, comprising a polypeptide or a protease-digested polypeptide with an amount of a coupling compound as claimed in claim 1;
   coupling polypeptides in the sample to a second member of the bio-orthogonal coupling pair linked to a substrate;
   optionally washing polypeptides bound to the substrate to remove any unbound materials from the substrate-bound polypeptides; and
   eluting the polypeptides from the substrate in an elution solution having an acidic pH.

3. The method of claim 2, wherein the substrate is a bead, a solid surface or a porous matrix.

4. The method of claim 2, wherein:
   the first member of the bio-orthogonal coupling pair is the tetrazinyl group, and the second member of the bio-orthogonal coupling pair is a strained cycloalkene.

5. The method of claim 2, wherein the polypeptides of the sample are digested with a modified trypsin polypeptide, comprising:
   a trypsin polypeptide;
   biotin moieties attached to the trypsin polypeptide; and
   groups comprising a member of a bio-orthogonal coupling pair attached to the trypsin polypeptide,
   wherein the ratio of groups comprising a member of a bio-orthogonal coupling pair to biotin moieties on the trypsin polypeptide ranges from 1:4 to 1:6.

6. The method of claim 4, wherein the strained cycloalkene is trans-cyclooctene.

* * * * *

UNITED STATES PATENT AND TRADEMARK OFFICE
CERTIFICATE OF CORRECTION

| | | |
|---|---|---|
| PATENT NO. | : 11,655,271 B2 | Page 1 of 2 |
| APPLICATION NO. | : 16/972923 | |
| DATED | : May 23, 2023 | |
| INVENTOR(S) | : Jonathan Minden et al. | |

It is certified that error appears in the above-identified patent and that said Letters Patent is hereby corrected as shown below:

In the Specification

1. Column 10, Lines 61-65, delete " 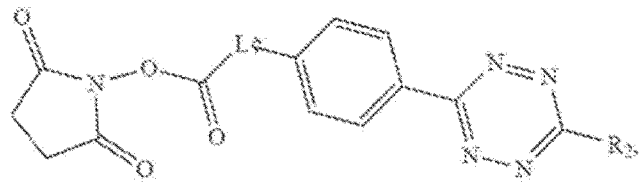 " and insert

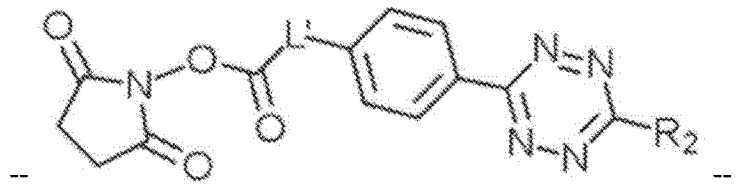 --

2. Column 11, Lines 25-29, delete " 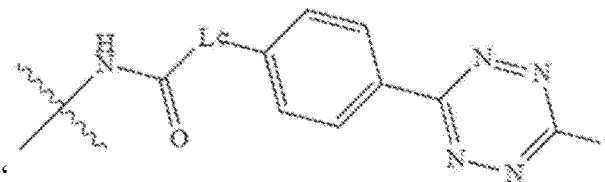 " and insert

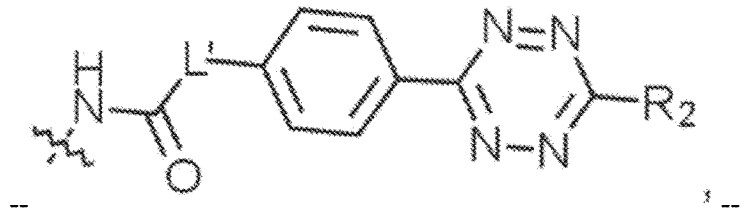 --

3. Column 21, Line 19, delete "0 ·" and insert -- "0X" --

4. Column 21, Line 19, delete "21 ·" and insert -- "21X" --

Signed and Sealed this
Tenth Day of October, 2023

*Katherine Kelly Vidal*

Katherine Kelly Vidal
*Director of the United States Patent and Trademark Office*

CERTIFICATE OF CORRECTION (continued)
U.S. Pat. No. 11,655,271 B2

5. Column 21, Line 19, delete "45 ·" and insert -- "45X" --

6. Column 21, Line 19, delete "75 ·" and insert -- "75X" --

7. Column 21, Line 19, delete "100 ·" and insert -- "100X" --

8. Column 22, Line 35, delete "0 ·" and insert -- "0X" --

9. Column 22, Line 36, delete "21 ·" and insert -- "21X" --

10. Column 22, Line 37, delete "45 ·" and insert -- "45X" --

11. Column 22, Line 38, delete "75 ·" and insert -- "75X" --

In the Claims

12. Column 23, Lines 36-50, Claim 1, delete " 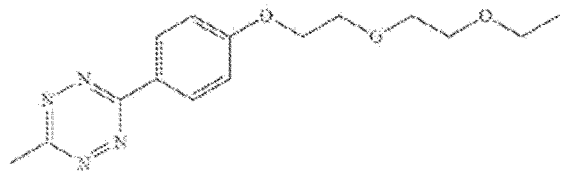 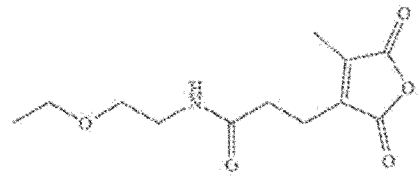 " and insert -- 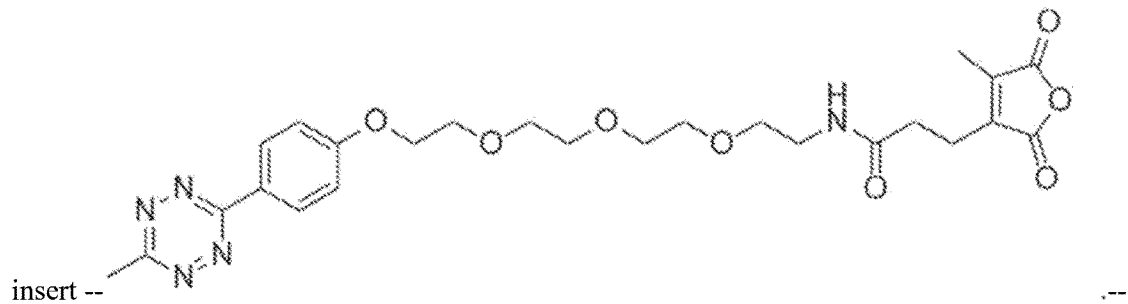 .--

SEQUENCE LISTING

```
<160> NUMBER OF SEQ ID NOS: 1

<210> SEQ ID NO 1
<211> LENGTH: 231
<212> TYPE: PRT
<213> ORGANISM: Sus scrofa

<400> SEQUENCE: 1

Phe Pro Thr Asp Asp Asp Lys Ile Val Gly Gly Tyr Thr Cys Ala
1               5                   10                  15

Ala Asn Ser Ile Pro Tyr Gln Val Ser Leu Asn Ser Gly Ser His Phe
            20                  25                  30

Cys Gly Gly Ser Leu Ile Asn Ser Gln Trp Val Val Ser Ala Ala His
        35                  40                  45
```

```
Cys Tyr Lys Ser Arg Ile Gln Val Arg Leu Gly Glu His Asn Ile Asp
    50              55                  60

Val Leu Glu Gly Asn Glu Gln Phe Ile Asn Ala Ala Lys Ile Ile Thr
65                  70                  75                  80

His Pro Asn Phe Asn Gly Asn Thr Leu Asp Asn Asp Ile Met Leu Ile
                85                  90                  95

Lys Leu Ser Ser Pro Ala Thr Leu Asn Ser Arg Val Ala Thr Val Ser
            100                 105                 110

Leu Pro Arg Ser Cys Ala Ala Ala Gly Thr Glu Cys Leu Ile Ser Gly
        115                 120                 125

Trp Gly Asn Thr Lys Ser Ser Gly Ser Ser Tyr Pro Ser Leu Leu Gln
    130                 135                 140

Cys Leu Lys Ala Pro Val Leu Ser Asp Ser Ser Cys Lys Ser Ser Tyr
145                 150                 155                 160

Pro Gly Gln Ile Thr Gly Asn Met Ile Cys Val Gly Phe Leu Glu Gly
                165                 170                 175

Gly Lys Asp Ser Cys Gln Gly Asp Ser Gly Gly Pro Val Val Cys Asn
            180                 185                 190

Gly Gln Leu Gln Gly Ile Val Ser Trp Gly Tyr Gly Cys Ala Gln Lys
        195                 200                 205

Asn Lys Pro Gly Val Tyr Thr Lys Val Cys Asn Tyr Val Asn Trp Ile
    210                 215                 220

Gln Gln Thr Ile Ala Ala Asn
225             230
```